US011460405B2

(12) United States Patent
Espinoza Vallejos et al.

(10) Patent No.: US 11,460,405 B2
(45) Date of Patent: Oct. 4, 2022

(54) MULTI-Z IMAGING AND DISPENSING WITH MULTI-WELL DEVICES

(71) Applicant: TAKARA BIO USA, INC., Mountain View, CA (US)

(72) Inventors: Patricio A. Espinoza Vallejos, Mountain View, CA (US); Syed A. Husain, Mountain View, CA (US); Chun-Wah Lin, Mountain View, CA (US); Hermann Hubschle, Mountain View, CA (US)

(73) Assignee: Takara Bio USA, Inc., San Jose, CA (US)

(*) Notice: Subject to any disclaimer, the term of this patent is extended or adjusted under 35 U.S.C. 154(b) by 989 days.

(21) Appl. No.: 16/091,068

(22) PCT Filed: Jul. 20, 2017

(86) PCT No.: PCT/US2017/043169
§ 371 (c)(1),
(2) Date: Oct. 3, 2018

(87) PCT Pub. No.: WO2018/017892
PCT Pub. Date: Jan. 25, 2018

(65) Prior Publication Data
US 2019/0113457 A1   Apr. 18, 2019

Related U.S. Application Data

(60) Provisional application No. 62/365,173, filed on Jul. 21, 2016.

(51) Int. Cl.
| | |
|---|---|
| *G01N 21/64* | (2006.01) |
| *B01J 19/00* | (2006.01) |
| *B01L 7/00* | (2006.01) |
| *G01N 15/14* | (2006.01) |
| *G01N 21/25* | (2006.01) |
| *G06T 11/00* | (2006.01) |
| *G06T 7/00* | (2017.01) |
| *G06V 20/69* | (2022.01) |
| *B01L 3/00* | (2006.01) |
| *C12Q 1/6844* | (2018.01) |

(52) U.S. Cl.
CPC .......... *G01N 21/6458* (2013.01); *B01J 19/00* (2013.01); *B01J 19/0046* (2013.01); *B01L 3/5085* (2013.01); *B01L 7/52* (2013.01); *C12Q 1/6844* (2013.01); *G01N 15/1463* (2013.01); *G01N 21/253* (2013.01); *G01N 21/6428* (2013.01); *G01N 21/6452* (2013.01); *G06T 7/0008* (2013.01); *G06T 11/00* (2013.01); *G06V 20/693* (2022.01); *B01J 2219/00315* (2013.01); *B01J 2219/00693* (2013.01); *B01J 2219/00702* (2013.01); *B01J 2219/00722* (2013.01); *B01J 2219/00743* (2013.01); *B01L 2200/0647* (2013.01); *B01L 2300/0829* (2013.01); *G01N 2021/6439* (2013.01); *G01N 2201/12* (2013.01); *G06T 2200/21* (2013.01); *G06T 2207/30072* (2013.01)

(58) Field of Classification Search
CPC .......... G01N 21/6458; G01N 15/1463; G01N 21/253; G01N 21/6428; G01N 21/6452; G01N 2021/6439; G01N 2201/12; G01N 35/1016; G01N 21/11; B01J 19/00; B01J 19/0046; B01J 2219/00315; B01J 2219/00693; B01J 2219/00702; B01J 2219/00722; B01J 2219/00743; B01L 3/5085; B01L 7/52; B01L 2200/0647; B01L 2300/0829; C12Q 1/6844; G06T 7/0008; G06T 11/00; G06T 2200/21; G06T 2207/30072; G06V 20/693; G06V 20/695; C12M 23/02; G02B 2207/113; G02B 21/367; G02B 27/0075
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |

(Continued)

FOREIGN PATENT DOCUMENTS

| | | | |
|---|---|---|---|
| CN | 1818051 A | 8/2006 | |
| CN | 1888880 A | 1/2007 | |

(Continued)

OTHER PUBLICATIONS

Harkness et al "High-content imaging with micropaterned multiwell plates reveals influence of cell geometry and cytoskeleton on chromatin dynamics" Biotechnology Journal Jun. 12, 2015, 10: 1555-1567. (Year: 2015).*

Agrawal, S. ed. Methods in Molecular Biology, "Protocols of Oligonucleotides and Analogs," vol. 20, 1993, Cover Pages and Table of Contents, pp. i-xiv (12 pages).

Beier, M. et al. "Versatile Derivatisation of Solid Support Media for Covalent Bonding on DNA-microchips," Nucleic Acids Research. May 1, 1999. vol. 27. No. 9, pp. 1970-1977.

(Continued)

*Primary Examiner* — Narayan K Bhat
(74) *Attorney, Agent, or Firm* — Andrew R. Guzman; Bret E. Field; Bozicevic, Field & Francis LLP

(57) ABSTRACT

Provided are methods, devices, assemblies, and systems for dispensing into the wells of a multi-well device and imaging such wells from multiple Z-planes. Multi-Z imaging of the present methods and systems may allow for the detection of wells of a multi-well device that contain a desired number of cells. Also provided are methods, devices, assemblies, and systems for processing cell-containing wells of a multi-well device identified through the use of multi-Z imaging.

9 Claims, 7 Drawing Sheets

(56) References Cited

U.S. PATENT DOCUMENTS

| | | |
|---|---|---|
| 4,965,188 A | 10/1990 | Mullis et al. |
| 5,106,584 A | 4/1992 | Funakubo |
| 5,130,238 A | 7/1992 | Malek et al. |
| 5,210,015 A | 5/1993 | Gelfand et al. |
| 5,252,294 A | 10/1993 | Kroy et al. |
| 5,270,184 A | 12/1993 | Walker et al. |
| 5,281,516 A | 1/1994 | Stapleton et al. |
| 5,338,671 A | 8/1994 | Scalice et al. |
| 5,342,581 A | 8/1994 | Sanadi |
| 5,399,491 A | 3/1995 | Kacian et al. |
| 5,455,166 A | 10/1995 | Walker |
| 5,475,610 A | 12/1995 | Atwood et al. |
| 5,480,784 A | 1/1996 | Kacian et al. |
| 5,494,810 A | 2/1996 | Barany et al. |
| 5,496,517 A | 3/1996 | Pfost et al. |
| 5,498,392 A | 3/1996 | Wilding et al. |
| 5,525,300 A | 6/1996 | Danssaert et al. |
| 5,552,321 A | 9/1996 | Focht |
| 5,552,580 A | 9/1996 | Pfost et al. |
| 5,587,128 A | 12/1996 | Wilding et al. |
| 5,589,136 A | 12/1996 | Northup et al. |
| 5,593,838 A | 1/1997 | Zanzucchi et al. |
| 5,602,756 A | 2/1997 | Atwood et al. |
| 5,639,423 A | 6/1997 | Northup et al. |
| 5,656,493 A | 8/1997 | Mullis et al. |
| 5,674,743 A | 10/1997 | Ulmer |
| 5,695,934 A | 12/1997 | Brenner |
| 5,714,330 A | 2/1998 | Brenner et al. |
| 5,716,842 A | 2/1998 | Baier et al. |
| 5,720,923 A | 2/1998 | Haff et al. |
| 5,721,136 A | 2/1998 | Finney et al. |
| 5,750,341 A | 5/1998 | Macevicz |
| 5,773,258 A | 6/1998 | Birch et al. |
| 5,779,977 A | 7/1998 | Haff et al. |
| 5,779,981 A | 7/1998 | Danssaert et al. |
| 5,824,518 A | 10/1998 | Kacian et al. |
| 5,827,480 A | 10/1998 | Haff et al. |
| 5,866,345 A | 2/1999 | Wilding et al. |
| 5,912,148 A | 6/1999 | Eggerding |
| 5,939,312 A | 8/1999 | Baier et al. |
| 5,955,029 A | 9/1999 | Wilding et al. |
| 5,985,555 A | 11/1999 | Bertling |
| 6,015,674 A | 1/2000 | Woudenberg et al. |
| 6,033,880 A | 3/2000 | Haff et al. |
| 6,054,263 A | 4/2000 | Danssaert et al. |
| 6,126,804 A | 10/2000 | Andresen |
| 6,130,073 A | 10/2000 | Eggerding |
| 6,132,580 A | 10/2000 | Mathies et al. |
| 6,153,426 A | 11/2000 | Heimberg et al. |
| 6,157,692 A | 12/2000 | Christensen et al. |
| 6,174,675 B1 | 1/2001 | Chow et al. |
| 6,184,029 B1 | 2/2001 | Wilding et al. |
| 6,197,572 B1 | 3/2001 | Schneebeli |
| 6,210,891 B1 | 4/2001 | Nyren et al. |
| 6,225,061 B1 | 5/2001 | Becker |
| 6,258,568 B1 | 7/2001 | Nyren |
| 6,284,525 B1 | 9/2001 | Mathies et al. |
| 6,303,343 B1 | 10/2001 | Kopf-sill |
| 6,306,590 B1 | 10/2001 | Mehta et al. |
| 6,306,597 B1 | 10/2001 | Macevicz |
| 6,309,886 B1 | 10/2001 | Ambrose et al. |
| 6,337,435 B1 | 1/2002 | Chu et al. |
| 6,406,893 B1 | 6/2002 | Knapp et al. |
| 6,420,143 B1 | 7/2002 | Kopf-sill |
| 6,423,536 B1 | 7/2002 | Javanovich et al. |
| 6,423,948 B1 | 7/2002 | Kwasnoski et al. |
| 6,432,360 B1 | 8/2002 | Church |
| 6,432,695 B1 | 8/2002 | Zou et al. |
| 6,444,461 B1 | 9/2002 | Knapp et al. |
| 6,448,066 B1 | 9/2002 | Wheatcroft |
| 6,485,944 B1 | 11/2002 | Church |
| 6,503,750 B1 | 1/2003 | Benett et al. |
| 6,509,186 B1 | 1/2003 | Zou et al. |
| 6,511,803 B1 | 1/2003 | Church et al. |
| 6,524,532 B1 | 2/2003 | Northup et al. |
| 6,524,830 B2 | 2/2003 | Kopf-sill |
| 6,537,799 B2 | 3/2003 | Chow et al. |
| 6,541,274 B2 | 4/2003 | Nagel et al. |
| 6,551,841 B1 | 4/2003 | Wilding et al. |
| 6,576,459 B2 | 6/2003 | Miles et al. |
| 6,586,233 B2 | 7/2003 | Benett et al. |
| 6,602,473 B1 | 8/2003 | Northup et al. |
| 6,605,213 B1 | 8/2003 | Ammann et al. |
| 6,656,724 B1 | 12/2003 | Heimberg et al. |
| 6,657,169 B2 | 12/2003 | Brown et al. |
| 6,660,517 B1 | 12/2003 | Wilding et al. |
| 6,670,153 B2 | 12/2003 | Stern |
| 6,677,151 B2 | 1/2004 | Sandell |
| 6,699,713 B2 | 3/2004 | Benett et al. |
| 6,703,236 B2 | 3/2004 | Atwood et al. |
| 6,730,883 B2 | 4/2004 | Brown |
| 6,756,019 B1 | 6/2004 | Dubrow et al. |
| 6,762,049 B2 | 7/2004 | Zou et al. |
| 6,767,512 B1 | 7/2004 | Lurz et al. |
| 6,787,308 B2 | 9/2004 | Balasubramanian et al. |
| 6,814,934 B1 | 11/2004 | Higuchi |
| 6,818,395 B1 | 11/2004 | Quake et al. |
| 6,830,936 B2 | 12/2004 | Anderson et al. |
| 6,833,246 B2 | 12/2004 | Balasubramanian |
| 6,875,602 B2 | 4/2005 | Guiterrez |
| 6,911,345 B2 | 6/2005 | Quake et al. |
| 6,962,821 B2 | 11/2005 | Danssaert et al. |
| 7,005,617 B2 | 2/2006 | Brown |
| 7,008,789 B2 | 3/2006 | Gambini et al. |
| 7,030,340 B2 | 4/2006 | Knoche |
| 7,051,536 B1 | 5/2006 | Cohen et al. |
| 7,074,367 B2 | 7/2006 | Lurz et al. |
| 7,133,726 B1 | 11/2006 | Atwood et al. |
| 7,164,077 B2 | 1/2007 | Venkatasubramaniam |
| 7,169,560 B2 | 1/2007 | Lapidus et al. |
| 7,183,103 B2 | 3/2007 | Gambini et al. |
| 7,238,321 B2 | 7/2007 | Witter et al. |
| 7,282,337 B1 | 10/2007 | Harris |
| 7,311,794 B2 | 12/2007 | Joseph et al. |
| 7,329,492 B2 | 2/2008 | Hardin et al. |
| 7,417,726 B2 | 8/2008 | Kao et al. |
| 7,429,479 B2 | 9/2008 | Harding et al. |
| 7,460,223 B2 | 12/2008 | Harding et al. |
| 7,482,120 B2 | 1/2009 | Buzby |
| 7,501,245 B2 | 3/2009 | Quake et al. |
| 7,504,241 B2 | 3/2009 | Atwood et al. |
| 7,547,556 B2 | 6/2009 | Hunter et al. |
| 7,560,273 B2 | 7/2009 | Sandell |
| 7,611,674 B2 | 11/2009 | Heimberg et al. |
| 7,668,697 B2 | 2/2010 | Volkov et al. |
| 7,771,933 B2 | 8/2010 | Arciniegas et al. |
| 7,833,709 B2 | 11/2010 | Joseph et al. |
| 8,252,581 B2 | 8/2012 | Joseph et al. |
| 8,481,292 B2 | 7/2013 | Casbon et al. |
| 8,835,358 B2 | 9/2014 | Fodor et al. |
| 9,097,702 B2 | 8/2015 | Fischbach |
| 9,132,427 B2 | 9/2015 | Joseph et al. |
| 9,447,925 B2 | 9/2016 | Griswold et al. |
| 9,828,576 B2 | 11/2017 | Viasnoff |
| 2001/0055765 A1 | 12/2001 | O'keefe et al. |
| 2002/0030044 A1 | 3/2002 | Brown |
| 2002/0060156 A1 | 5/2002 | Mathies et al. |
| 2002/0068357 A1 | 6/2002 | Mathies et al. |
| 2002/0072112 A1 | 6/2002 | Atwood et al. |
| 2002/0072113 A1 | 6/2002 | Barbera-Guillem et al. |
| 2002/0110899 A1 | 8/2002 | Wheatcroft |
| 2002/0127660 A1 | 9/2002 | Danssaert |
| 2002/0144771 A1 | 10/2002 | Kuczynski |
| 2002/0182544 A1 | 12/2002 | Chan-Park et al. |
| 2003/0006003 A1 | 1/2003 | Matsuoka |
| 2003/0008286 A1 | 1/2003 | Zou et al. |
| 2003/0032048 A1 | 2/2003 | Kim et al. |
| 2003/0032191 A1 | 2/2003 | Hilson et al. |
| 2003/0040011 A1 | 2/2003 | Barth et al. |
| 2003/0040104 A1 | 7/2003 | Barbera-Guillem |
| 2003/0138829 A1 | 7/2003 | Unger et al. |
| 2003/0138941 A1 | 7/2003 | Gong et al. |
| 2003/0157509 A1 | 8/2003 | Mirzabekov et al. |
| 2003/0199081 A1 | 10/2003 | Wilding et al. |

(56) References Cited

U.S. PATENT DOCUMENTS

| | | |
|---|---|---|
| 2003/0214994 A1 | 11/2003 | Schicke et al. |
| 2003/0219788 A1 | 11/2003 | Kaltenboeck |
| 2004/0001861 A1 | 1/2004 | Sandell |
| 2004/0029303 A1 | 2/2004 | Hart et al. |
| 2004/0060917 A1 | 4/2004 | Liu et al. |
| 2004/0072334 A1 | 4/2004 | Benett et al. |
| 2004/0096958 A1 | 5/2004 | Pottathil et al. |
| 2004/0123880 A1 | 7/2004 | Chiles et al. |
| 2004/0185504 A1 | 9/2004 | Pantoliano et al. |
| 2004/0209331 A1 | 10/2004 | Ririe |
| 2004/0258568 A1 | 12/2004 | Lurz et al. |
| 2005/0019792 A1 | 1/2005 | McBride et al. |
| 2005/0112634 A1 | 5/2005 | Woudenberg et al. |
| 2005/0129581 A1 | 6/2005 | McBride et al. |
| 2005/0145273 A1 | 7/2005 | Atwood et al. |
| 2005/0176155 A1 | 8/2005 | Klein et al. |
| 2005/0130173 A1 | 9/2005 | Leamon et al. |
| 2005/0225751 A1 | 10/2005 | Sandell et al. |
| 2005/0233324 A1 | 10/2005 | Corbett et al. |
| 2006/0024831 A1 | 2/2006 | Kao et al. |
| 2006/0027317 A1 | 2/2006 | Joseph et al. |
| 2006/0030035 A1 | 2/2006 | Joseph et al. |
| 2006/0030036 A1 | 2/2006 | Joseph et al. |
| 2006/0030037 A1 | 2/2006 | Joseph et al. |
| 2006/0046265 A1 | 3/2006 | Becker et al. |
| 2006/0046304 A1 | 3/2006 | Shigeura et al. |
| 2006/0073491 A1 | 4/2006 | Joseph et al. |
| 2006/0088931 A1 | 4/2006 | Ririe |
| 2006/0094108 A1 | 5/2006 | Yoder |
| 2006/0166226 A1 | 7/2006 | Kudoh et al. |
| 2006/0205064 A1 | 9/2006 | Tajima |
| 2006/0239980 A1 | 10/2006 | Bernard |
| 2006/0246493 A1 | 11/2006 | Jensen et al. |
| 2006/0270026 A1 | 11/2006 | Soh et al. |
| 2007/0020640 A1 | 1/2007 | Mccloskey et al. |
| 2007/0084279 A1 | 4/2007 | Huang et al. |
| 2007/0290282 A1 | 12/2007 | Belov et al. |
| 2008/0026483 A1 | 1/2008 | Oldenburg |
| 2008/0176290 A1 | 7/2008 | Joseph et al. |
| 2008/0240542 A1 | 10/2008 | Queeney et al. |
| 2008/0241951 A1 | 10/2008 | Batiulga et al. |
| 2008/0288179 A1 | 11/2008 | Kao et al. |
| 2008/0299651 A1 | 12/2008 | Atwood et al. |
| 2009/0026082 A1 | 1/2009 | Rothberg et al. |
| 2009/0035777 A1 | 2/2009 | Kokoris et al. |
| 2009/0061513 A1 | 3/2009 | Andersson Svahn et al. |
| 2009/0127589 A1 | 5/2009 | Rothberg et al. |
| 2009/0214616 A1 | 8/2009 | Elbert |
| 2010/0137143 A1 | 6/2010 | Rothberg et al. |
| 2010/0233698 A1 | 9/2010 | Joseph et al. |
| 2010/0246927 A1* | 9/2010 | Arbuckle ............... G06V 20/69 359/385 |
| 2010/0301398 A1 | 12/2010 | Rothberg et al. |
| 2012/0010091 A1 | 1/2012 | Linnarson |
| 2013/0296535 A1 | 11/2013 | Church et al. |
| 2014/0130885 A1 | 5/2014 | Griswold et al. |
| 2014/0233797 A1 | 8/2014 | Hodder et al. |
| 2014/0363838 A1* | 12/2014 | Mcdevitt ............ G01N 33/5005 435/29 |
| 2015/0299784 A1 | 10/2015 | Fan et al. |
| 2015/0364307 A1 | 12/2015 | Agar et al. |
| 2016/0010151 A1 | 1/2016 | Fan et al. |
| 2016/0145683 A1 | 5/2016 | Fan et al. |
| 2016/0245813 A1* | 8/2016 | Mir ..................... C12Q 1/06 |
| 2016/0265069 A1 | 9/2016 | Fan et al. |
| 2016/0289729 A1* | 10/2016 | Richards ................ B01L 3/527 |
| 2017/0237894 A1* | 8/2017 | Hikida ..................... G02B 7/38 348/79 |
| 2019/0136176 A1* | 5/2019 | Kawachi ................ C12M 41/14 |

FOREIGN PATENT DOCUMENTS

| | | |
|---|---|---|
| CN | 102046773 A | 5/2011 |
| CN | 102289066 A | 12/2011 |
| CN | 104307581 A | 1/2015 |
| EP | 0438883 B1 | 5/1996 |
| EP | 0881489 | 12/1996 |
| EP | 0637999 B1 | 12/1998 |
| EP | 0739423 B1 | 1/2002 |
| EP | 0684315 | 6/2002 |
| EP | 1022059 B1 | 8/2002 |
| EP | 1157744 B1 | 3/2004 |
| EP | 1013342 B1 | 4/2004 |
| EP | 0881950 B1 | 7/2004 |
| EP | 0871545 B1 | 1/2005 |
| EP | 1510823 A2 | 3/2005 |
| EP | 0733098 B1 | 1/2006 |
| EP | 1539353 B1 | 2/2006 |
| EP | 2278548 | 1/2011 |
| GB | 2370112 A | 6/2002 |
| JP | 2002-010777 A | 1/2002 |
| JP | 2002-355090 A | 12/2002 |
| JP | 2003-014753 A | 1/2003 |
| JP | 3696141 B2 | 9/2005 |
| JP | 2006-223309 A | 8/2006 |
| JP | 2015-108837 A | 6/2015 |
| JP | 2015-130805 A | 7/2015 |
| JP | 2015-130806 A | 7/2015 |
| WO | WO 96/15269 A2 | 5/1996 |
| WO | WO 97/042500 A1 | 11/1997 |
| WO | WO 2000018957 | 4/2000 |
| WO | WO0127635 A1 | 4/2001 |
| WO | WO 2005/028109 A2 | 3/2002 |
| WO | WO 2001/009389 A2 | 2/2003 |
| WO | WO 2004013604 | 2/2004 |
| WO | WO 2005/028110 A2 | 3/2005 |
| WO | WO 2005/028629 A2 | 3/2005 |
| WO | WO 2005/108604 A2 | 11/2005 |
| WO | WO 2006084132 | 8/2006 |
| WO | WO 2006/102264 A1 | 9/2006 |
| WO | WO 2006127191 | 11/2006 |
| WO | WO 2009/083648 A2 | 7/2009 |
| WO | WO 2009/100933 A1 | 8/2009 |
| WO | WO 2010022391 | 2/2010 |
| WO | WO 2010/140982 A1 | 12/2010 |
| WO | WO 2014201272 | 12/2014 |
| WO | WO 2014201273 | 12/2014 |
| WO | WO 2015031691 | 3/2015 |

OTHER PUBLICATIONS

Guschin, D. et al. "Manual Manufacturing of Oligonucleotide, DNA, and Protein Microchips," Analytical Biochemistry. Aug. 1, 1997. vol. 250. No. 2, pp. 203-211.

Innis et al. "Optimization of PCRs," In: PCR Protocols (Innis, Gelfand, Sninsky and White, eds.). Academic Press, New York. 1990; pp. 3-12.

Joos, B. et al. "Covalent Attachment of Hybridizable Oligonucleotides to Glass Supports," Analytical Biochemistry, Apr. 5, 1997, vol. 247, No. 1, pp. 96-101.

Lin et al. "Fabrication of polydimethylsiloxane (PDMS) pulsating heat pipe," Applied Thermal Engineering. 2009; 29(2-3), pp. 573-580.

Mcpherson et al. eds. The series Methods in Enzymology (Academic Press, Inc.): PCR 2: A practical approach. Oxford University Press, New York, 1995, 332 pages.

Nagai et al., "High-throughput PCR in silicon based mircochamber array" Biosensors & Bioelectrics 2001, vol. 16, pp. 1015-1019.

Quirk et al. Semiconductor Manufacturing Technology, Prentice Hall, NJ, 2001, 67 pages.

Rychlik et al. "Optimization of the annealing temperature for DNA amplification in vitro," Nucleic Acids Research 1990; 18 (21):6409-6412.

Sambrook et al. Molecular Cloning: A Laboratory Manual, 2nd Edition, 1989, 1546 pages.

Wolf, S. Silicon Processing for the VLSI Era, vol. 1-4, Lattice Press, 2002, 822 pages.

Yoon et al. "Precise temperature and rapid thermal cycling in a micromachined DNA polymerase chain reaction chip" J. Micromech. Microeng. 2002, 12, pp. 813-823.

(56) References Cited

OTHER PUBLICATIONS

Mitra et al., Fluorescent in situ sequencing on polymerase colonies. Anal Biochem. Sep. 1, 2003;320(1):55-65.

Morozova et al., Applications of next-generation sequencing technologies in functional genomics. Genomics. Nov. 2008;92(5):255-64.

Mullis et al., Specific synthesis of DNA in vitro via a polymerase-catalyzed chain reaction. Methods Enzymol. 1987;155:335-50.

Adessi et al., Solid phase DNA amplification: characterisation of primer attachment and amplification mechanisms. Nucleic Acids Res. Oct. 15, 2000;28(20):E87.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Bennett et al., Toward the 1,000 dollars human genome. Pharmacogenomics. Jun. 2005;6(4):373-82.

Bontoux et al., Integrating whole transcriptome assays on a lab-on-a-chip for single cell gene profiling. Lab Chip. Mar. 2008;8(3):443-50.

Craig et al., Identification of genetic variants using bar-coded multiplexed sequencing. Nat Methods. Oct. 2008;5(10):887-93.

Esumi et al., Method for single-cell microarray analysis and application to geneexpression profiling of GABAergic neuron progenitors. Neurosci Res. Apr. 2008;60(4):439-51.

Genome Analysis: Analyzing DNA, vol. 1, eds. Birren et al., Dec. 1997, TOC only, 13 Pages.

Guatelli et al., Isothermal, in vitro amplification of nucleic acids by a multienzyme reaction modeled after retroviral replication. Proc Natl Acad Sci USA. Mar. 1990;87(5):1874-8.

Hollas (Lecture Notes in Computer Science vol. 2812, 2003, pp. 55-62.

Hug et al., Measurement of the number of molecules of a single mRNA species in a complex mRNA preparation. J Theor Biol. Apr. 21, 2003;221(4):615-24.

Krebs et al., Molecular analysis of circulating tumour cells-biology and biomarkers. Nat Rev Clin Oncol. Mar. 2014;11(3):129-44.

Kwoh et al., Transcription-based amplification system and detection of amplified human immunodeficiency virus type 1 with a bead-based sandwich hybridization format. Proc Natl Acad Sci USA. Feb. 1989;86(4):1173-7.

Lizardi et al., Exponential Amplification of Recombinant-RNA Hybridization Probes. Nat Biotechnol. 1988;6:1197-1202.

Maclean et al., Application of 'next-generation' sequencing technologies to microbial genetics. Nat Rev Microbial. Apr. 2009;7(4):287-96.

Margulies et al., Genome sequencing in microfabricated high-density picolitre reactors. Nature. Sep. 15, 2005;437(7057):376-80.

Murakawa et al., Direct detection of HIV-1 RNA from AIDS and ARC patient samples. DNA. May 1988;7(4):287-95.

Parameswaran et al., A pyrosequencing-tailored nucleotide barcode design unveils opportunities for large-scale sample multiplexing. Nucleic Acids Res. 2007;35(19):e130.

Qui et al., DNA sequence-based "bar codes" for tracking the origins of expressed sequence tags from a maize cDNA library constructed using multiple mRNA sources. Plant Physiol. Oct. 2003;133(2):475-81.

Shendure et al., Accurate multiplex polony sequencing of an evolved bacterial genome. Science. Sep. 9, 2005;309(5741):1728-32.

Soumillon et al., Characterization of directed differentiation by high-throughput single-cell RNA-Seq. http://dx.doi.org/10.1101/003236, Mar. 5, 2014, 13.

Sutcliffe et al., TOGA: an automated parsing technology for analyzing expression of nearly all genes. Proc Natl Acad Sci U S A. Feb. 29, 2000;97(5):1976-81.

Voelkerding et al., Next-generation sequencing: from basic research to diagnostics. Clin Chem. Apr. 2009;55(4):641-58.

Walker et al., Isothermal in vitro amplification of DNA by a restriction enzyme/DNA polymerase system. Proc Natl Acad Sci US A. Jan. 1, 1992;89(1):392-6.

Weiss, Hot prospect for new gene amplifier. Science. Nov. 29, 1991;254(5036):1292-3.

International Search Report and Written Opinion for PCT /US2016/018823, dated Apr. 29, 2016, 8 pages.

Bjork (Dissertation, 2014, pp. 1-108).

Gad et al. (Safety Evaluation in the Development of Medical Devices and Combination Products, Third Edition, Chapter 12, 2008, pp. 151-180).

Collins, et al. "The The Poisson 1-15 distribution and beyond: methods for microfluidic droplet production and single cell encapsulation", Lab on a Chip, vol. 15, No. 17, 2015, pp. 3439-3459.

Kachouie, et al. "Arraycount, an algorithm for automatic cell counting in microwell arrays", Biotechniques Rapid Dispatches, Informa Healthcare, US, vol. 47, No. 3, 2009, 8 pages.

Communication pursuant to Article 94(3) EPC for European patent application No. 08 713 240.3, dated Mar. 5, 2018, 7 pages.

Communication, Extended European search report p for European application No. 16753205.0, dated Jun. 11, 2018, 9. pages.

* cited by examiner

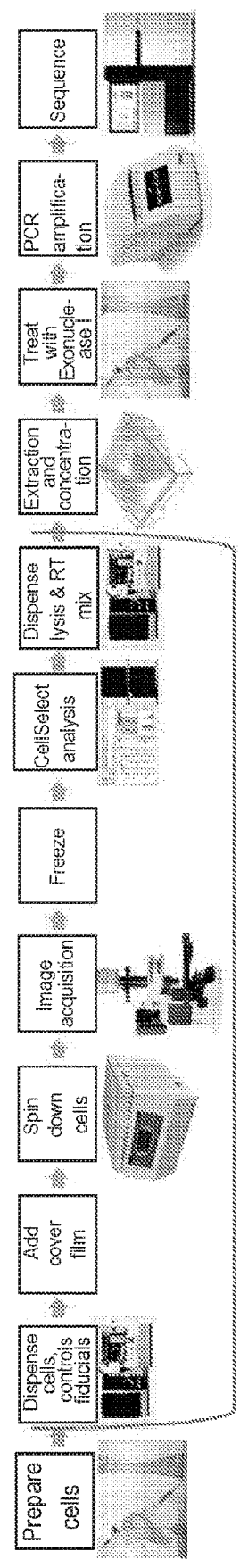
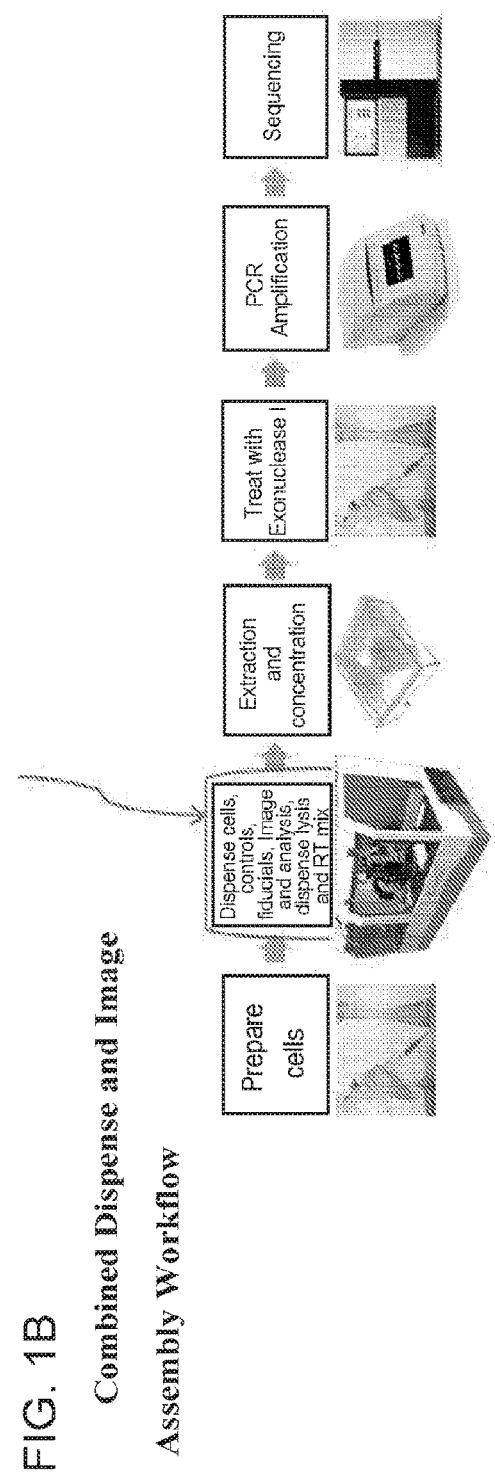
FIG. 1A Non-Condensed Work Flow
FIG. 1B Combined Dispense and Image Assembly Workflow

MULTI-Z IMAGING AND DISPENSING WITH MULTI-WELL DEVICES

CROSS-REFERENCE TO RELATED APPLICATIONS

Pursuant to 35 U.S.C. § 119 (e), this application claims priority to the filing date of the U.S. Provisional Patent Application Ser. No. 62/365,173, filed Jul. 21, 2016; the disclosure of which application is herein incorporated by reference.

INTRODUCTION

Geneticists are striving to characterize complex diseases like cancer, autoimmune and neurological disorders, but finding the underlying mechanisms driving these diseases has been elusive. Somatic mutations, spontaneous variants that accumulate in cells over a lifetime, are a major factor that drives disease onset and reoccurrence. As cells accumulate new mutations, they form polyclonal cell populations that co-exist with normal cells. Sequencing bulk cell populations can mask the underlying heterogeneity of these unique rare cell types, making it difficult to distinguish them from normal germline mutations. The best way to reveal these differences and visualize the clonal architecture is to sequence individual cells in the population.

SUMMARY

Provided are methods, devices, assemblies, and systems for dispensing into the wells of a multi-well device and imaging such wells from multiple Z-planes. Multi-Z imaging of the present methods and systems may allow for the detection of wells of a multi-well device that contain a desired number of cells. Also provided are methods, devices, assemblies, and systems for processing cell-containing wells of a multi-well device identified through the use of multi-Z imaging.

In certain embodiments, provided herein are systems comprising: a) a dispense and image assembly comprising: i) a liquid dispensing component, and ii) an image acquisition component capable of focusing and generating images at different z-planes above a multi-well device, and b) a movement component configured to move said dispense and image assembly. In other embodiments, systems and method are provided for imaging wells comprising: i) capturing a plurality of images from different z-planes (e.g., 10 . . . 30 . . . or more) above a multi-well device, ii) determining the minimum number of different z-planes (e.g., 2-15) that are required in order to generate a composite image that provides an in-focus image of all of the cells present in the wells.

In some embodiments, provided herein are methods for imaging wells of a multi-well chip comprising: a) providing: i) a first multi-well device comprising a plurality of wells containing a first volume of aqueous solution, wherein at least 1% . . . 5% . . . 20% . . . 30% . . . 40% . . . 50% . . . or 60% of the plurality of wells contain either only one or only two cells (e.g., at least 35% of the wells contain a single cell), and ii) an image acquisition system capable of focusing and generating images at different z-planes, and iii) optionally a second multi-well device (e.g., that is the same device as the first device, including same well geometry) comprising a plurality of wells containing the first volume of an aqueous solution, wherein at least 1% . . . 5% . . . 20% . . . 30% . . . 40% . . . 50% . . . or 60% of the plurality of wells contain either only one or only two cells; b) capturing a plurality of images (e.g., 3 . . . 10 . . . 100 . . . 1000 or more images) from different z-planes above the multi-well device of a first portion (e.g., 8 wells of a 100 well or 5000 well device) of the plurality of wells using the image acquisition system configured with a first set of imaging parameters; c) determining the Zmax plane and the Zmin plane from the different z-planes, wherein the Zmax plane is the plane farthest from the multi-well device that contains a least one cell in focus, and wherein the Zmin plane is the plane closest to the multi-well device that contains at least one cell in focus; d) determining the minimum number of the different z-planes (e.g., 2, or 3 or 4 . . . 10 . . . 15 . . . or more) that are required to capture images from in order to generate a composite image that provides an in-focus image of all of the cells present in the first portion of the plurality of wells, wherein the minimum number of the different z-planes includes at least the Zmax and the Zmin planes; and e) performing at least one of the following: i) imaging, with the image acquisition system, a second portion (e.g., 92 wells of a 100 well device) of the plurality of wells of the multi-well device using only the minimum number of different z-planes; and/or ii) imaging at least a portion of the second multi-well device with an image acquisition system configured with the first set of imaging parameters, wherein the imaging uses only the minimum number of different z-planes. In general, the deeper the wells in the multi-well device, the more z-planes (besides Zmax and Zmin) need to be employed for generating images.

In certain embodiments, the methods further comprise, in step e) generating a composite image from images taken at the minimum number of different z-planes. In other embodiments, the methods comprise, after step e) determining the number cells present in each of the wells in the second portion of the first multi-well device, and/or determining the number of cells present in each of the wells in the portion of the second multi-well device. In other embodiments, the minimum number of different z-planes further includes one, two, three, or four z-planes between the Zmax and Zmin planes. In additional embodiments, the minimum number of different z-planes only includes the Zmax and the Zmin planes. In particular embodiments, the minimum number of different z-planes includes only the Zmax plane, the Zmin plane, and one other plane (and only one other plane) between the Zmax and Zmin planes. In certain embodiments, deeper wells require at least two more (e.g., exactly two more planes) besides Zmax and Z min planes.

In some embodiments, the imaging parameters comprise a first magnification (e.g., 2×, 3×, 4× . . . 15× . . . 50× . . . 100× . . . 250× . . . or more). In certain embodiments, the imaging parameters comprise a first numerical aperture. In other embodiments, the image acquisition system further comprises a light source (e.g., UV light, laser light, or other light used for excitation of fluorescent dyes). In particular embodiments, the cells are stained with one or more fluorescent stains. In some embodiments, cells are fluorescently tagged by using fluorescently conjugated antibodies that bind to the cell membrane. In particular embodiments, the fluorescent stains are selected from Hoechst stain and Propidium Iodide.

In certain embodiments, the image acquisition system further comprises a liquid dispensing component configured to add the aqueous solution to the plurality of wells. In other embodiments, the liquid dispensing component is configured to dispense a dispense volume of the aqueous solution into each of the plurality of wells, wherein the aqueous solution comprises cells present in the aqueous solution at a concentration such that, on average X cell(s) is/are present in the dispense volume. In particular embodiments, X is 1, 2, 3, 4, 5, or more.

In some embodiments, the plurality of wells in the first and/or second multi-well device is at least 95 . . . 100 . . . 200 . . . 500 . . . 1000 . . . 3000 . . . 5000 . . . 10,000 or more wells (e.g., nano or micro wells). In certain embodiments, the second multi-well device is not provided. In other embodiments, a dispensing map is generated that indicate which wells contain only a single cell (e.g., a single live cell or a single dead cell), and which wells contain either zero or more than one live or dead cell. In particular embodiments, the first volume of aqueous of solution is between 25 nl and 2 µl. In other embodiments, each of the wells has a volume between 25 nl and 2 µl. In further embodiments, each of the wells has a volume between 50 nl and 500 nl.

In some embodiments, provided herein are multi-purpose systems comprising: a) a multi-well device securing component configured to secure a multi-well device in a fixed position, wherein the multi-well device comprises a plurality of wells; b) a dispense and image assembly comprising: i) a liquid dispensing component configured to dispense liquid into the wells of a multi-well device, and ii) an image acquisition component capable of focusing and generating images at different z-planes above the multi-well device, wherein the image acquisition component is attached to, or adjacent to, the liquid dispending component, and c) a movement component configured to move the dispense and image assembly with respect to the multi-well device such that, when the multi-well device is in the fixed position, most or all of the plurality of wells in the multi-well device: i) are able to receive liquid from the liquid dispensing component, and ii) are able to be imaged by the image acquisition component.

In certain embodiments, the liquid dispensing component is configured to dispense a dispense volume of liquid into each of the plurality of wells, wherein the liquid comprises cells present in the liquid at a concentration such that, on average X cell(s) is/are present in the dispense volume. In particular embodiments, X is 0.01, 0.02, 0.1, 0.5, 1, 2, 3, 4, 5, or more. In some embodiments, the system further comprises the multi-well device. In certain embodiments, the plurality of wells in the first multi-well device is at least 100 wells (e.g., 100 . . . 500 . . . 1000 . . . 5000 or more). In further embodiments, the image acquisition component further comprises a light source. In particular embodiments, each of the plurality of wells has a volume between 25 nl and 2 µl. In other embodiments, each of the plurality of wells has a volume between 50 nl and 500 nl. In further embodiments, the movement component comprises a first rail to move the dispense and image assembly in the X direction and a second rail to move the dispense and image assembly in the Y direction. In other embodiments, the systems further comprise a computer component comprising computer memory and a computer processor, wherein instructions on the computer memory control: i) the movement of the movement component, ii) the liquid dispensing of the dispense component, and iii) the image capture of the image acquisition component.

In certain embodiments, provided herein are methods comprising: a) providing: i) a multi-well device comprising a plurality of wells, and ii) a multi-well device securing component configured to secure a multi-well device in a fixed position, wherein the multi-well device comprises a plurality of wells, iii) multi-purpose system comprising: A) a dispense and image assembly comprising: I) a liquid dispensing component configured to dispense liquid into the wells of a multi-well device, and II) an image acquisition component capable of focusing and generating images at different z-planes above the multi-well device, wherein the image acquisition component is attached to, or adjacent to, the liquid dispending component, and B) a movement component configured to move the dispense and image assembly with respect to the multi-well device; b) placing the multi-well device in the securing component such the multi-well device is located at the fixed position; and c) activating the dispense and image assembly such that most or all of the plurality of wells in the multiwall device: i) receive cell-containing liquid from the liquid dispensing component such that at least 1% . . . 5% . . . 20% . . . 30% . . . 50% of the plurality of wells contains either only one cell or only two cells, and ii) are imaged by the image acquisition component at a plurality of z-planes above the bottom of the multi-well device thereby generating a plurality of images from different z-planes.

In particular embodiments, the methods further comprise: d) determining the Zmax plane and the Zmin plane from the different z-planes, wherein the Zmax plane is the plane farthest from the multi-well device that contains a least one cell in focus, and wherein the Zmin plane is the plane closest to the multi-well device that contains at least one cell in focus. In certain embodiments, the methods further comprise: e) determining the minimum number of the different z-planes that are required (e.g., 2-15) to capture images from in order to generate a composite image that provides an in-focus image of all of the cells present in the plurality of wells, wherein the minimum number of the different z-planes includes at least the Zmax and the Zmin planes.

In certain embodiments, the multi-well device comprises at least 50 wells (e.g., 50 . . . 100 . . . 150 . . . 400 . . . 689 . . . 900 . . . or more). In additional embodiments, the multi-well device comprises at least 1000 wells (e.g., 1000 . . . 1500 . . . 2500 . . . 5000 . . . 5184 . . . 10,000 . . . 20,000 . . . or more). In other embodiments, the multi-well device comprises a multi-well chip.

In particular embodiments, the methods further comprise labeling at least some of the cells with a first and/or second detectable label before and/or after the dispensing in step. In certain embodiments, the first or second detectable label is specific for circulating cancer cells and/or cancer stem cells. In other embodiments, the first or second detectable label comprises an antibody or an antigen binding portion of an antibody. In some embodiments, the cells in the cell suspension are purified from tumor tissue. In other embodiments, the dispensing volume is between 25 nl and 500 nl or between 500 nl and 1 µl. In further embodiments, the labeling of the cells is before the dispensing. In further embodiments, the labeling of the cells is after the dispensing.

BRIEF DESCRIPTION OF THE FIGURES

FIG. 1A shows an exemplary work flow that does not employ a combined dispensing and imaging assembly, while FIG. 1B shows a similar exemplary work flow employing a combined dispensing and imaging assembly. The work flow in 1B shows that certain steps can be avoided in some embodiments of the present methods, such as centrifugation and freezing.

DETAILED DESCRIPTION

Provided are methods, devices, assemblies, and systems for dispensing into the wells of a multi-well device and imaging such wells from multiple Z-planes. Multi-Z imaging of the present methods and systems may allow for the detection of wells of a multi-well device that contain a desired number of cells. Also provided are methods, devices, assemblies, and systems for processing cell-containing wells of a multi-well device identified through the use of multi-Z imaging.

In certain embodiments, provided herein are systems comprising: a) a dispense and image assembly comprising: i) a liquid dispensing component, and ii) an image acquisition component capable of focusing and generating images at different z-planes above a multi-well device, and b) a movement component configured to move said dispense and image assembly. In other embodiments, systems and method are provided for imaging wells comprising: i) capturing a plurality of images from different z-planes (e.g., 10 . . . 30 . . . or more above a multi-well device, ii) determining the minimum number of different z-planes that are required (e.g., 2-15) in order to generate a composite image that provides an in-focus image of all of the cells present in the wells.

Provided herein, in certain embodiments, are integrated systems that, for example, significantly simplify the single cell workflow by combining imaging and dispensing steps by providing an assembly with dispensing and imaging capabilities. Having the dispenser and the imaging system on the same instruments can significantly reduce the need for handling of a multi-well device (e.g., a SMARTCHIP™ multi-well device as sold by WAFERGEN (WaferGen Bio-systems, Inc.)) by an operator. In addition, employing multiple z-plane images above the multi-well device allows for certain advantages in some embodiments. For example, multi-z-plane imaging may allow for more accurate detection of candidate wells of a multi-well device that contain a desired number of cells or the simplification of sample processing including e.g., the removal of one or more process steps including e.g., the removal of a centrifugation step.

An example of a simplified process is shown in FIG. 1. FIG. 1A shows an exemplary work flow that does not employ a combined dispensing and imaging assembly, while FIG. 1B shows a similar exemplary work flow employing a combined dispensing and imaging assembly. The work flow in 1B shows that certain steps can be avoided in some embodiments of the herein described methods, such as centrifugation and freezing.

An Exemplary Workflow

Figure 2:
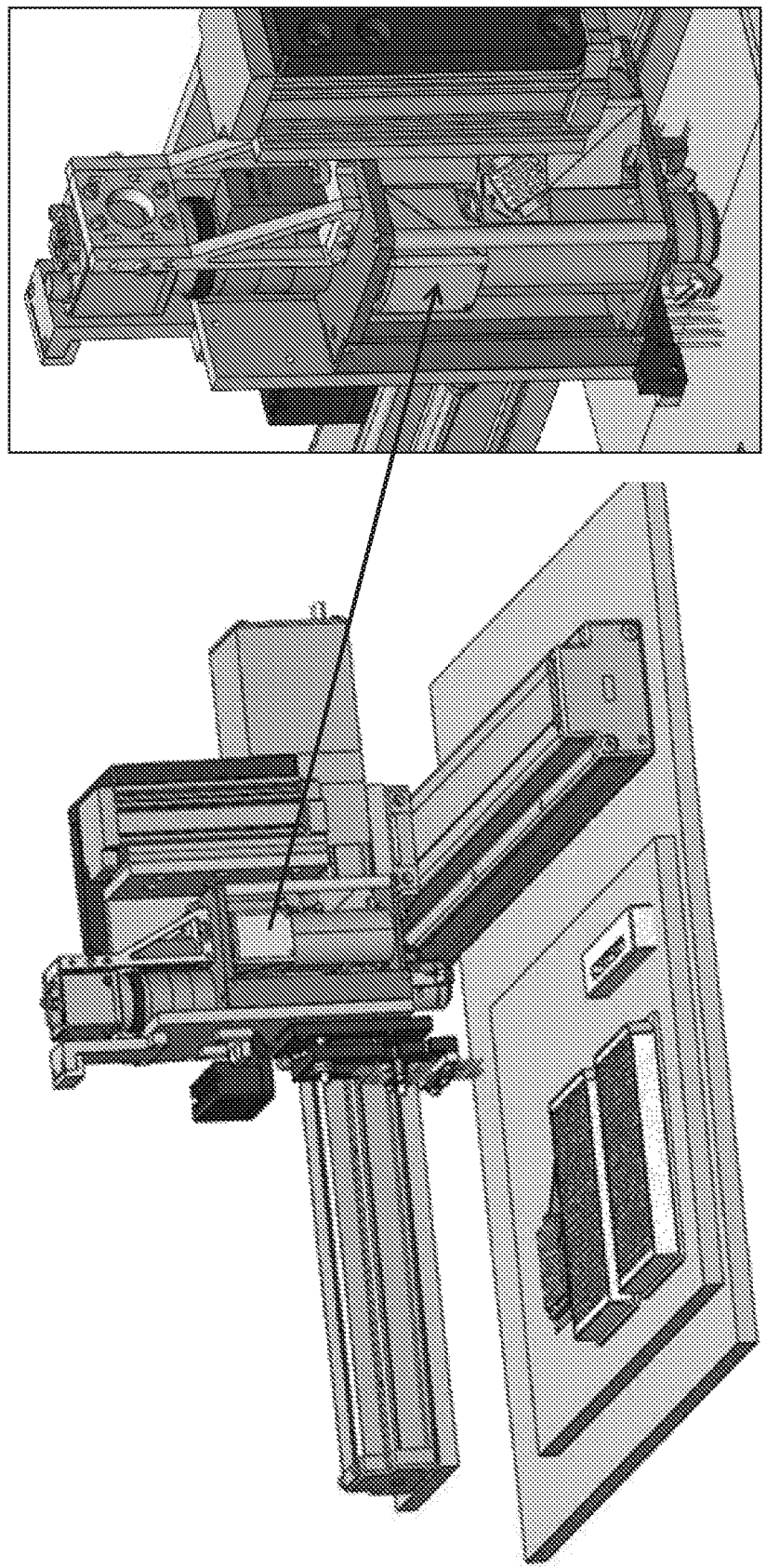
FIG. 2 shows an exemplary combined dispensing and imaging assembly, which is carried on a movement component, which is shown as two rails in this embodiment.

The following work flow steps are employed in an exemplary embodiment when using an integrated dispenser and imaging assembly (e.g., one with multi-Z capability). First, fluorescently stained cells are preloaded in a 384-well plate. In this exemplary embodiment, eight samples can be dispensed into a multi-well device (e.g., SMARTCHIP™ multi-well device as sold by WAFERGEN (WaferGen Bio-systems, Inc.), which contains 5184 wells). FIG. 2 shows an exemplary integrated system that can dispense and image cells, along with a movement component for automatically moving the integrated system above the multi-well device. The system depicted in FIG. 2 includes two movement components ("rails") and an integrated imaging and dispense system (inset), wherein the dispense system includes a plurality of dispense tips. The integration of the imaging components with the dispense components allows for coordination between the detection of candidate cell-containing wells, as performed using the imaging system, with the dispense of cells into the wells and subsequent addition of processing reagents, if applicable, as performed using the dispense system.

In work conducted during the development of embodiments of the present disclosure, multiple cell lines were used, including K562 cells and dispense volumes of the order of 50 nL were employed using the dispenser multi-sample nano-dispenser (MSND+) as sold by WAFERGEN (WaferGen Bio-systems, Inc.). When dispensing cell suspension in the subject multi-well systems according to these embodiments, the concentration of the cell solution may be configured such that, on average, only one cell is dispensed per well.

In the subject embodiment, after dispensing, the multi-well chips are imaged using one or more wavelengths of light (including where one or more wavelengths of light are employed that correspond to the excitation wavelength of particular fluorescent dye(s) or fluorophore containing molecule(s) present in, with or attached to the cells) and multiple Z-planes. An instrument used in this exemplary workflow has the capability of focusing at different z-planes. In the exemplary embodiment, there are three filter sets available for scanning, and examples provided of work conducted during development of embodiments of this disclosure employed two of the filters. In such instances, one filter was used for identifying the cell (e.g., based on nuclear staining) and another to assess the health of the cell membrane (e.g., based on exclusion of a live cell-impermeable DNA intercalating dye).

Next the cells are imaged by the integrated dispense and image assembly. Imaging of cells generally requires magnification, which leads to reduced deep of field $d_{tot}$. The equation that follows shows this mathematically. The equation also shows that high numerical aperture decreases the depth of field $d_{tot}$. However, higher numerical aperture is generally desirable because it increases the sensitivity.

$$d_{tot} = \frac{\lambda n}{NA^2} + \frac{n}{MNA}e$$

Where:
$d_{tot}$: depth of field,
$\lambda_0$: wavelength,
n: refractive index,
NA: Numerical aperture
M: Objective magnification
e: imaging resolution When imaging thousands of discrete objects or cells that may be located at different Z-planes, it is important that all the objects are accurately imaged. This is especially important for single cell applications where only a single cell is to be identified. Therefore, provided herein, are methods and systems to improve the ability to identify cells in microwells or other cell capture devices. In this exemplary embodiment, first the imaging device is used to scan the wells of a multi-well device (e.g., a SMARTCHIP™ multi-well device as sold by WAFERGEN (WaferGen Bio-systems, Inc.) or other cell capture device) at multiple focal points or Z-planes. Then, a composite image is created by selecting the pixels of each image that are more in focus. This can be done using an extended focus algorithm. Once the composite image is obtained, the resulting image can be processed by cell counting software, such as CELLSELECT™ software (as sold by WAFERGEN (WaferGen Bio-systems, Inc.)) to accurately count all the cells in the capturing device (e.g., a SMARTCHIP™ multi-well device as sold by WAFERGEN (WaferGen Bio-systems, Inc.)). This procedure can be used with images obtained with any imaging mode such as transmission, reflection, fluorescence, etc.

Figure 3A:
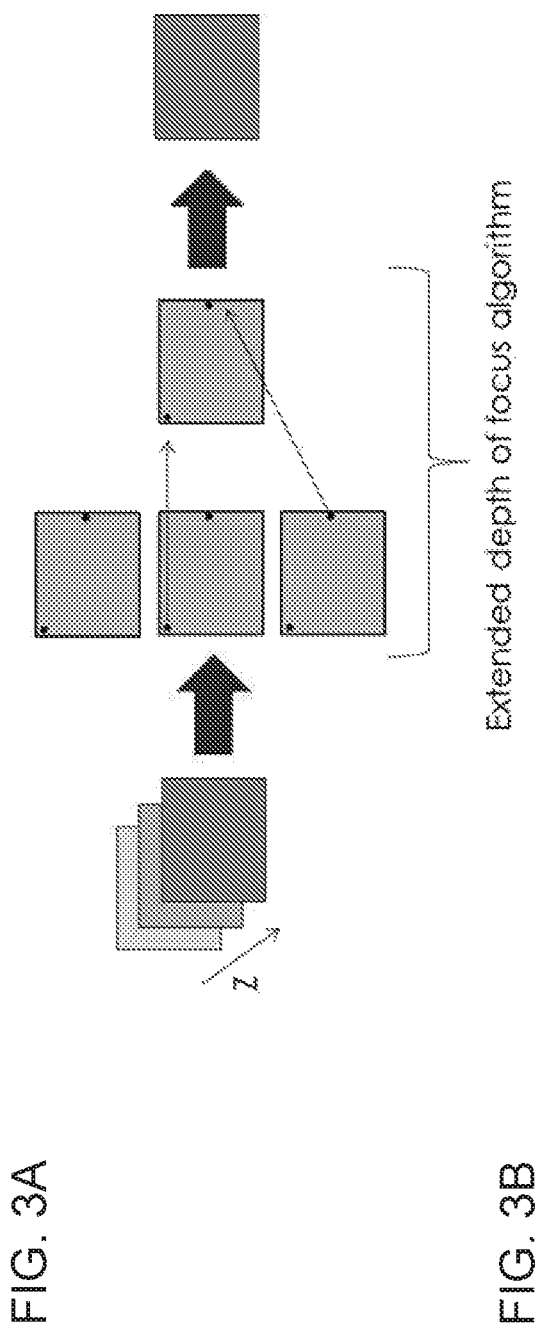
FIG. 3A shows a schematic of an exemplary extended depth of focus algorithm, depicting how multiple images at different depths are taken and then combined to provide a composite image with all of the cells in focus.
Figure 3B:
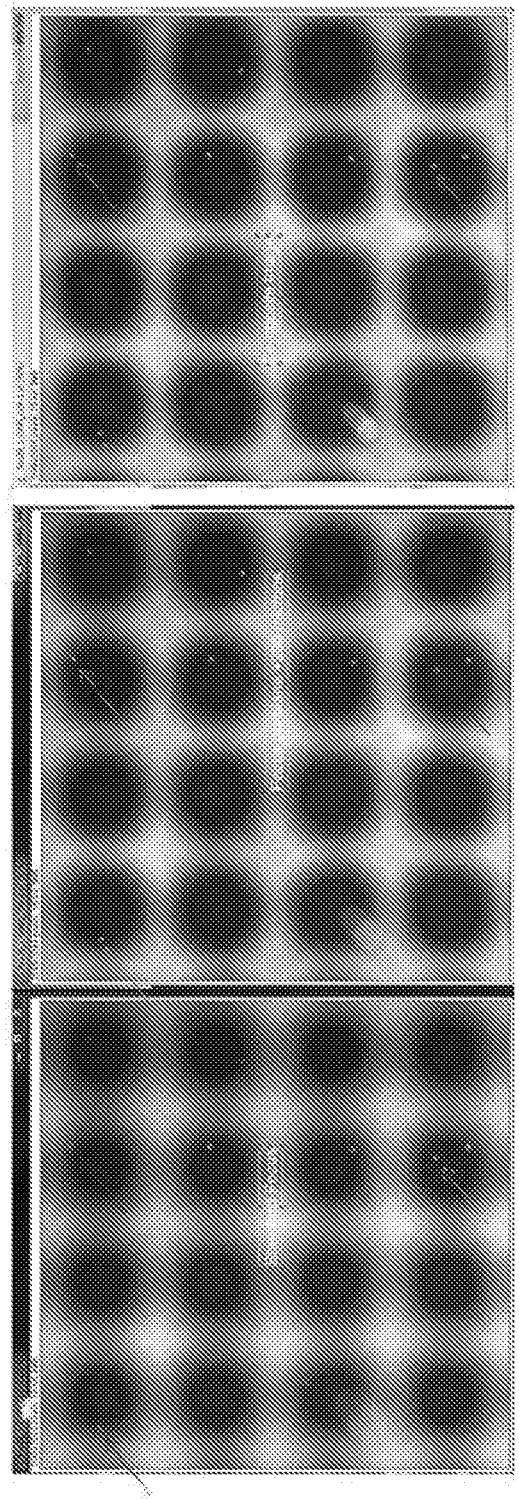
FIG. 3B shows a first image of 16 wells in a chip, where some of the cells are in focus, and a second image of the same 16 wells that is 200 microns higher (different Z-plane) with other cells in focus. The third image is a composite of the first two images, showing all the single and double cells in focus in the wells.

An example of how an extended focus algorithm can work is shown in FIG. 3. FIG. 3A shows a schematic of an exemplary extended depth of focus algorithm, depicting how multiple images at different depths are taken and then combined to provide a composite image with all of the cells in focus. FIG. 3B shows a first image of 16 wells in a chip, where some of the cells are in focus, and a second image of the same 16 wells that is 200 microns higher (different Z-plane) with other cells in focus. The third image is a composite of the first two images, showing all the single and double cells in focus in the wells. In FIG. 3B, some of the cells of the image on the left are slightly out of focus and they are indicated with darker arrows, while other cells are in focus and indicated with lighter arrows. The image in the center was obtained by increasing the distance from the microscope objective to the sample by 200 microns. In this case, some of the cells became in focus but others became out of focus. The third image shows the result of an extended depth of filed algorithm. This new image is a composite of the previous two images, and it can be observed that all the cells show good focus when compared to the original images.

Now that the most in focus cells have been identified, a cell detection algorithm such as CELLSELECT™ (WAFERGEN (WaferGen Bio-systems, Inc.)) can be used to identify wells with one cell, no cells, two cells, or other numbers of cells. In this regard, a dispense map may be generated by such software to indicate which wells have cells or a desired number of cells, for example a single cell, and should receive reagents for processing the cell(s) (e.g., reagents to lyse the cell(s), amplify nucleic acid(s), and sequence the nucleic acid(s), etc.).

Elements of the above described exemplary workflow need not necessarily be present in all embodiments. As such, other embodiments may include or exclude one or more elements of the above described exemplary workflow and the exemplary workflow may be modified, e.g., to include, or provide in the alternative, one or more elements described herein.

Multi-Z-Plane Imaging

Aspects of the methods, devices, assemblages and systems described herein may make use of multi-z-plane imaging. By "multi-z-plane imaging" is meant imaging of a single field that is performed at multiple imaging distances from the object or objects being imaged. Such multiple imaging distances may be referred to as z-distances and each z-distance may define a z-plane. Given the shallow depth of field of most microscopic objective lenses, images taken at different z-planes will generally contain different qualities of focus for objects within the image. For example, a first image of two objects, that are at different distances from the objective lens, may place the first of the two objects in-focus and the second of the two objects out of focus. When a second image is taken at a different z-distance the first object may move out of focus and the second object may move into focus.

The distances between the multi-well device and an objective lens may be varied by any convenient process including but not limited to e.g., through moving the objective lens progressively closer to the multi-well device, by moving the objective lens progressively further from the multi-well device, by moving the multi-well device progressively closer to the objective lens, by moving the multi-well device progressively further from the objective lens, moving both the multi-well device and the objective lens, etc.

As compared to single-z-plane imaging, multi-z-plane imaging may increase the probability that a sufficiently in-focus image of all, most or many of the objects within the imaging field is acquired. Such may be the case when, e.g., the range of z-planes within which the objects may theoretically lie is greater than the depth of field of the objective lens used in the imaging.

Work conducted during development of embodiments of the present disclosure sought to evaluate a multi-Z, composite image approach. By "composite image" is generally meant an image constructed of two or more images. Multi-Z composite images will generally be constructed of multiple images taken of the same field where a z-distance adjustment is made between capturing the multiple images, including e.g., where z-distance adjustments are the only imaging parameter changed between capturing images employed in constructing a multi-Z composite image. Various methods may be employed for combining multiple images captured at a plurality of z-planes into a multi-Z composite image, including e.g., those described using one or more of the image processing approaches described in more detail below.

If it is assumed that a multi-Z or composite image is the most reliable measurement of the number of cells, one can use that image to evaluate the accuracy of the results obtained with the other images. In particular, it is of interest to compare the multi-Z image with the single Z-plane image that the user would obtain when manually focusing on the sample. Work conducted took 144 areas of interest (AOI) of a SMARTCHIP™ multi-well device at different z-planes, calculated the composite images, used CELLSELECT™ (WAFERGEN (WaferGen Bio-systems, Inc.)) cell counting software and obtained the sensitivity and specificity of the results obtained based on the single-Z image. In the following table (Table 1), a positive result is considered a well containing a single cell. If the well has more than one cell or if the well has no cells, the result is considered negative for that well.

TABLE 1

| FB Chip 75662<br>SW 1.1.10 V4 | Multi-Z<br>Single Cell | Multi-Z<br>Not Single Cell |
|---|---|---|
| Single-Z<br>Single Cell | 1431<br>TRUE POSITIVE | 125<br>FALSE POSITIVE |
| Single-Z<br>Not Single Cell | 93<br>FALSE NEGATIVE | 3518<br>TRUE NEGATIVE |
| Sensitivity** | | Specificity** |
| 93.9% | | 96.9% |

With this information, the user can modify the cell dispensing in order to obtain higher levels of specificity and sensitivity. Various algorithms can be used to generate the multi-Z image, such algorithms including e.g., those available in the literature (e.g., Microsc Res Tech. 2004 September; 65(1-2):33-42. Complex wavelets for extended depth-of-field: a new method for the fusion of multichannel microscopy images. Forster B, Van De Ville D, Berent J, Sage D, Unser M.; Extended depth of field using shapelet-based image analysis. Meneses J, Suarez M A, Braga J, Gharbi T. Appl Opt. 2008 Jan. 10; 47(2):169-78; and Model-based 2.5-d deconvolution for extended depth of field in brightfield microscopy, Aguet F, Van De Ville D, Unser M, all of which are herein incorporated by reference in their entireties). Additional methods and algorithms are provided herein that allow the fewest number of z-plane images necessary to identify wells containing a desired number of cells to be employed. Such methods and algorithms in many instances speed up and simplify multi-well sample processing.

Figure 4:
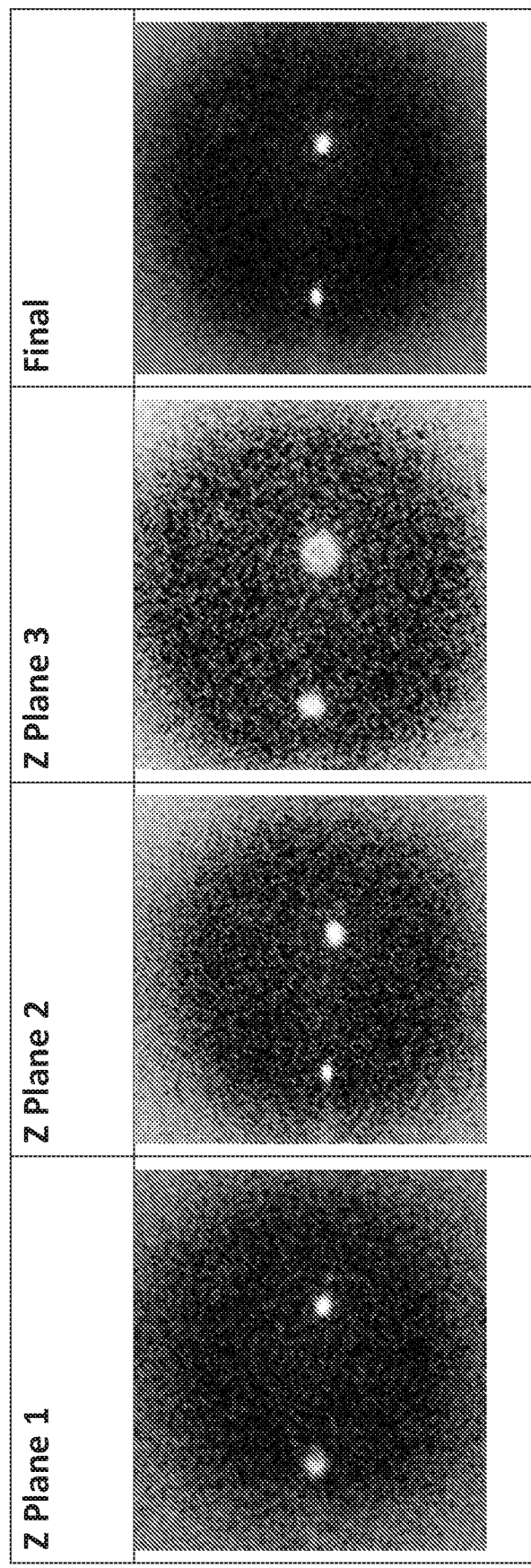
FIG. 4 shows different z-plane images of a single well (plane 1, plane 2, and plane 3), and then a composite image (Final image) that combines the three images.

FIG. 4 provides exemplary output of original and composite images using a method and algorithm disclosed herein. In particular, FIG. 4 shows different z-plane images of a single well ("z-plane 1", "z-plane 2", and "z-plane 3"), and then a composite image ("Final" image) generated from the three z-plane images. The actual number of z-plane images obtained and/or used in the subject methods and systems to identify candidate wells will vary and may depend on a number of factors including e.g., the volume of fluid within the wells, the size of the wells, the number of wells within the multi-well device, etc. Useful numbers of z-plane images may include but are not limited to e.g., 2 to 10 or more, including but not limited to e.g., 2 to 10, 2 to 9, 2 to 8, 2 to 7, 2 to 6, 2 to 5, 2 to 4, 3 to 10, 3 to 9, 3 to 8, 3 to 7, 3 to 6, 3 to 5, 4 to 10, 4 to 9, 4 to 8, 4 to 7, 4 to 6, 5 to 10, 5 to 9, 5 to 8, 5 to 7, 6 to 10, 6 to 9, 6 to 8, 7 to 10, 7 to 9, 8 to 10, 10, 9, 8, 7, 6, 5, 4, 3, 2, etc.

In addition to the number of z-planes utilized in multi-z-plane imaging, the z-distance between planes will vary and may depend on a number of factors including e.g., the number of z-planes employed, the volume of fluid within the wells, the size of the wells, the number of wells within the multi-well device, the depth of field of the imaging system, etc. In some instances, the z-distances between z-planes may range from less than 10 µm to 1 mm or more, including but not limited to e.g., 10 µm to 1 mm, 10 µm to 900 µm, 10 µm to 800 µm, 10 µm to 700 µm, 10 µm to 600 µm, 10 µm to 500 µm, 10 µm to 400 µm, 10 µm to 300 µm, 10 µm to 200 µm, 10 µm to 100 µm, 10 µm to 50 µm, 100 µm to 1 mm, 100 µm to 900 µm, 100 µm to 800 µm, 100 µm to 700 µm, 100 µm to 600 µm, 100 µm to 500 µm, 100 µm to 400 µm, 100 µm to 300 µm, 100 µm to 200 µm, etc.

Multi-z-plane imaging may be employed in various aspects of the methods, devices, assemblages, and systems described herein. For example, in some instances, multi-z-plane imaging may be employed in imaging all wells of a multi-well device, e.g., to allow for the identification of candidate wells (i.e., wells containing a desired number of cells) from all the wells of the multi-well device. Wells of a multi-well device may be imaged individually (i.e., one at a time) or multiple wells may be imaged within a single field of view (i.e., multiple wells may be imaged at the same time or simultaneously). The number of wells present in a single field of view when multiple wells are imaged will vary and may range from 2 to 100 or more, including but not limited to e.g., 2 to 100, 2 to 90, 2 to 80, 2 to 70, 2 to 60, 2 to 50, 2 to 40, 2 to 30, 2 to 20, 2 to 10, 10 to 100, 10 to 90, 10 to 80, 10 to 70, 10 to 60, 10 to 50, 10 to 40, 10 to 30, 10 to 20, and the like. In some instances, the batch imaging of wells of a multi-well device may be expressed in terms of the number of imaging fields employed to image all the wells of the device, where such number will vary and may range from 2 to 500 or more, including but not limited to e.g., 2 to 500, 2 to 400, 2 to 300, 2 to 200, 2 to 100, 2 to 50, 2 to 25, 2 to 10, 100 to 500, 100 to 400, 100 to 300, 100 to 200, 200 to 500, 200 to 400, 200 to 300, 10 to 100, 10 to 50, and the like.

In some instances, multi-z-plane imaging may be employed in determining the number of z-planes to be used in imaging the multi-well device. For example, a round of multi-z-plane imaging may utilized to collect multiple z-plane images of well of a multi-well device to determine the degree of z-plane sampling that would be sufficient to detect candidate wells with a desired sensitivity and specificity. Such multi-z-plane imaging performed in advance of the actual multi-z-plane imaging used to identify candidate wells may be referred to herein as "pilot-imaging". Pilot-imaging may involve imaging only a portion or sample of the wells of a multi-well device. The multiple-z-plane images obtained for the portion of wells of the device during pilot-imaging may then be used to determine how many z-planes are to be imaged for all of or the rest of the wells of the multi-well plate. In some instances, the parameters determined during pilot-imaging may be applied across the imaging of multiple similar multi-well devices.

Pilot-imaging may be performed at a higher or lower level of z-sampling as compared to the multi-z-plane imaging performed for all the wells of the device. For example, in some instances, a larger number of z-planes may be captured during pilot-imaging as compared to subsequent imaging. In some instances, a smaller number of z-planes may be captured during pilot-imaging as compared to subsequent imaging. In some instances, the same number of z-planes may be captured during pilot-imaging as compared to subsequent imaging. In some instances, pilot imaging may be employed to determine and/or set the level of the z-planes to be used in subsequent multi-z-plane imaging. For example, pilot imaging may be employed to determine the position of a Zmax and/or a Zmin z-plane utilized in subsequent multi-z-plane imaging.

In one embodiment, during pilot-imaging one or more wells may be imaged at a plurality of z-planes and the images may be analyzed to determine the lowest z-plane and the highest z-plane of the plurality that each contain an in-focus cell. Such lowest and highest z-planes may then be set as the Zmin and Zmax for subsequent imaging. In some instances, a margin of error may be incorporated into the setting of Zmin and Zmax, including e.g., where the Zmin and Zmax are set some z-distance from the lowest z-plane and the highest z-plane of the plurality that each contain an in-focus cell, including e.g., from 10 μm or less to 100 μm or more above or below, and the like. In some instances, a margin of error may be set to some fraction or multiple of the overall z-distance between the lowest z-plane and the highest z-plane of the plurality that each contain an in-focus cell, including e.g., ±10% of the distance, ±20% of the distance, ±30% of the distance, ±40% of the distance, ±50% of the distance, ±100% of the distance, ±200% of the distance, etc. In some instances, no margin for error may be introduced and the Zmin and Zmax may be set to the corresponding z-distances of the detected highest and lowest in-focus cells of the images captured during pilot-imaging.

Multi-z-plane imaging of the wells of the multi-well device (i.e., non-pilot imaging) may or may not include one or more of a determined Zmin and Zmax planes. In some instances, multi-z-plane imaging may include both the Zmin and Zmax planes, including where additional planes between the Zmin and Zmax planes are or are not included. In some instances, multi-z-plane imaging may exclude one or both of the Zmin and Zmax planes, including where only additional planes between the Zmin and Zmax planes are used. The number of planes used between the Zmin and Zmax planes, whether or not the Zmin and Zmax planes are used, will vary and may range from 1 to 10 or more including but not limited to e.g., 1 to 10, 1 to 9, 1 to 8, 1 to 7, 1 to 6, 1 to 5, 1 to 4, 1 to 3, 2 to 10, 2 to 9, 2 to 8, 2 to 7, 2 to 6, 2 to 5, 2 to 4, 3 to 10, 3 to 9, 3 to 8, 3 to 7, 3 to 6, 3 to 5, 4 to 10, 4 to 9, 4 to 8, 4 to 7, 4 to 6, 5 to 10, 5 to 9, 5 to 8, 5 to 7, 6 to 10, 6 to 9, 6 to 8, 7 to 10, 7 to 9, 8 to 10, 10, 9, 8, 7, 6, 5, 4, 3, 2, 1, etc.

Various z-planes described and utilized in the subject methods and systems may be defined relative to one another and/or based on their absolute positions, e.g., relative to the multi-well plate (including e.g., relative to the bottom of the wells of the multi-well plate), relative to the objective lens utilized in the imaging, and the like. For example, a Zmin plane, having an in-focus cell, may be at or X μm above the bottom of a well of the multi-well plate and a second z-plane may be described as being Y μm above the Zmin plane, etc.

Image Processing and Acquisition

Generated multi-z-plane images may be processed through various image processing steps and/or image processing algorithms. In some instances, generated multi-z-plane images may be processed to identify candidate wells of a multi-well device. In some instances, image processing of multi-z-plane images may include the production of a composite image, from which candidate well identification may be performed. In some instances, the generated multi-z-plane images may be used in identifying candidate wells of a multi-well plate without generating a composite image, e.g., candidate wells may be identified directly from the generated multi-z-plane images, e.g., through one or more image processing steps but without the production of a composite image. Various image processing steps may be performed in the individual images of a set of multi-z-plane images, a composite image generated from a set of multi-z-plane images or both.

Useful image processing steps may include but are not limited to e.g., mathematical image (i.e., pixel-wise) transformation (i.e., pixel-wise addition, subtraction, division, multiplication, etc.), statistical image transformations (e.g., median transform, standard deviation transform, etc.), smoothing algorithms, blur transform/filtering, morphological dilation, splitting channels of a multichannel image, generating one or more image masks, space filing or hole closing, noise filtering, segmentation, and the like. In some instances, two or more images may be combined in a particular image processing step, including where images or image transformations thereof are mathematically combined including e.g., summed, averaged, subtracted, etc. For example, in some instances, two or more images or transformations thereof may be combined to generate a weighted sum image, a sum of weighted images, or both or the like. In some instances, combining images may make use of a float image. In the context of the present methods and systems, in general a "float" image may refer to an image to which pixel values from multiple z-planes may be combined (e.g., added, subtracted, multiplied, etc.) without pixel intensity saturation, thus allowing an increase in the dynamic range (i.e., the float image may have a dynamic range that exceeds that of the individual images added to the float image). Various approaches to employing a float image may find use in the present methods and systems. Image processing steps may be applied globally across an entire image or may be applied selectively across one or more regions of interest (ROI) of the image. In some instances, the image processing steps employed in a subject algorithm may be limited only to globally applied image processing steps.

Image processing steps generally include the processing of digital images, which may vary and may be in binary (e.g., black and white), grayscale or color formats. Images of various formats may further be converted between formats, as desired, by suitable image processing algorithms. For example, a color image may be "split" into individual color channels to produce individual grayscale images for each color channel. For example, a red, green and blue image (RGB) image may be split into individual red, green and blue channels to produce a grayscale image of the red channel, a grayscale image of the green channel and a grayscale image of the blue channel. Color images may be converted between color spaces and split into any convenient and appropriate color channels of a particular color space including but not limited to e.g., RGB color space, CMYK color space, HSV color space, CIE color space, Lab color space, CIELUV color space, YCbCr color space, and the like. Binary images and grayscale images may be applied to a channel of a color image and, e.g., where multiple binary or grayscale images are applied to multiple channels of a color image, a color image may be constructed, or "merged", from binary and/or grayscale images.

Other digital image processing image transformations that may find use in the described methods include but are not limited to e.g., point processing transformations (e.g., negative transform, log transform, inverse log transform, nth root transform, nth power transform, gamma correction, contrast transforms, window center correction, histogram equalization, etc.), filtering (i.e., neighbor) transformations (e.g., mean filters, Gaussian filters, median filters, image gradient filters, Laplacian filters, normalized cross correlation (NCC) filters, etc.), and the like.

In some embodiments, a standard deviation image may be created for each z-plane image where every pixel of the standard deviation image represents the standard deviation of a grouping of neighboring pixels, e.g., the 5×5 neighborhood in the original image. Standard deviation image transformations may, in some instances, be similar to auto-focus transformations, except that standard deviation transformation is calculated for every pixel individually. Generally, in images containing cells, the standard deviation will be high in areas where there is a cell in focus and low elsewhere. Therefore, when the weighted average of a pixel is taken over all z-planes where the weight is the standard deviation, the plane that has the highest standard deviation will be weighted the most.

In some embodiments, amplification of a transformed image may be performed, e.g., to increase small differences between z-plane images. For example, in some embodiments the standard deviation transformed image may be amplified to increase the differences in standard deviation between z-planes. To amplify the weight of an in-focus pixel all standard deviation weights may be amplified, e.g., raised to the fourth power. Such amplification may result in a distribution of z-weights where most values are close to 0 (i.e., no objects in any of the z-planes) and, if there is an object visible in a portion of the z-planes, a portion of the values will be much greater than 0. Data amplification may not be limited to that described and, as such, may vary.

In some embodiments, image processing algorithms may take advantage of z-plane images produced where, generally, the out-of-focus pixels are darker than the in-focus pixels. Accordingly, in some instances, a produced weighted image (e.g., a standard deviation weighted image) may be multiplied by the original image or images to amplify the intensity of bright areas, increasing even more the contrast between the bright areas and background. Where such amplification is employed in combination with standard deviation weighting, the result may be weighted images having a dynamic range of several orders of magnitude. Background pixels that are not part of a cell at any z-plane will generally have weights that are the same or nearly the same for all planes and the final averaged values for the background pixels across all z-planes. Where low concentration cell dispensing is employed, the vast majority of pixels analyzed will have these characteristics of background pixels.

In some instances, image processing algorithms may include an image smoothing operation. Image smoothing may be employed, in some instances, to prevent e.g., where a first pixel having the majority of its weight in a first z-plane is neighbored by a pixel having the majority of its weight in a different z-plane. Smoothing may be beneficial in situations where images contain few cells and each cell is expected to be in best focus in one, or at most two, z-planes and there are essentially no objects (i.e., cells) that truly extend through more than two z-planes. Smoothing may be achieved by a variety of means including e.g., through the use of one or more float images. Float images may be stored in computer memory and successively supplied z-planes may be added to, or otherwise mathematically combined with, the float image. Various float images may be employed including e.g., a weighted sum float image, a sum of weights float image, and the like. In some instances, an algorithm may include two float images kept in memory, including e.g., a weighted sum image and a sum of weights image. Where float images are employed for smoothing, the float images may be updated for each z-plane that is supplied to the algorithm.

Composite images, also referred to as z-composite or flattened images, may be generated using a variety of image processing methods. In some instances, an image processing algorithm may be employed that includes the production of a float image and the composite image may be generated from the float image. In some instances, an image processing algorithm may be employed that includes the production of two or more float images and the composite image may be generated from a combination of the float images. For example, in some instances, the pixels of the generated flat image may be the weighted sum of the z-plane pixels divided by the sum of all weights for that pixel. Thus, regardless of whether the actual sum of all weights varies wildly from one pixel to the next, the relative z-weights for a given pixel coordinate are clearly discernable across the composite image and sufficient for detection by cell counting software.

Figure 5:
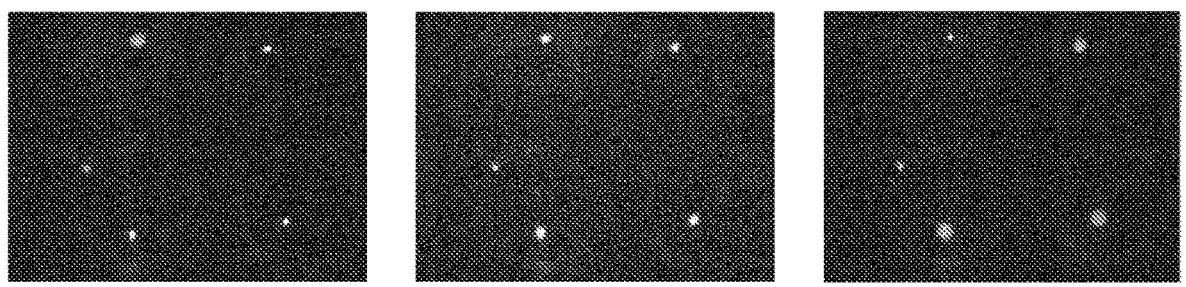
FIG. 5 provides multi-z-plane images of multiple wells of a multi-well device.
Figure 6:
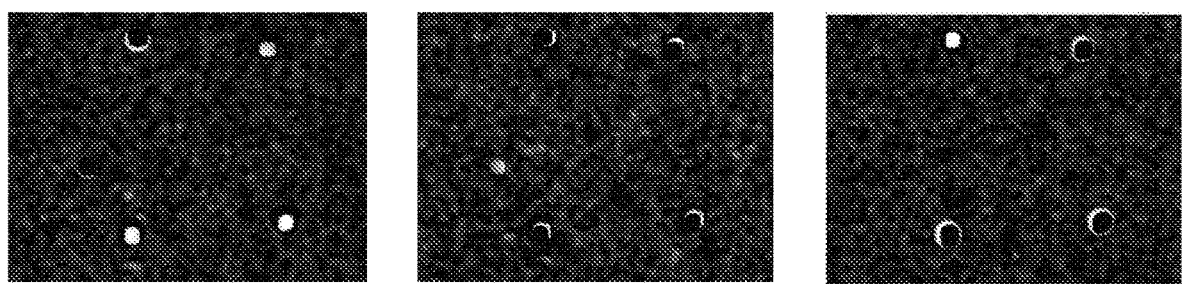
FIG. 6 depicts the multi-z-plane images of FIG. 5 weighted according to an image processing algorithm.
Figure 7:
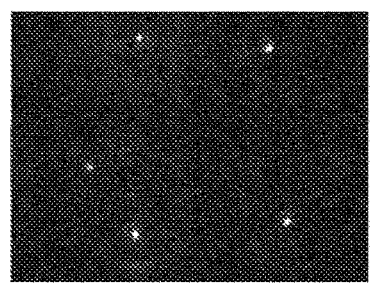
FIG. 7 provides a composite (i.e., flattened) image generated from the weighted multi-z-plane images of FIG. 6.

In an exemplary image processing algorithm, multiple z-plane images (FIG. 5) are provided to the algorithm and these images are weighted (FIG. 6) as described above. The weighted images are combined using a float image and the float image is flattened to produce a composite image (FIG. 7). Such a composite image may be utilized by cell counting software to identify the well having a desired number of cells and a map may be generated indicating which wells of the multi-well plate are to be further processed.

Images utilized in the herein described methods will be digital images, the types and acquisition of which may vary. A "digital image", as used herein, generally refers to a numeric representation (e.g., binary representation) of a two-dimensional image that may be of fixed or unfixed resolution. Fixed resolution images have a fixed number of rows and columns of pixels in an XY orientation. In some instances, digital images may be three-dimensional having fixed number of voxels in a XYZ orientation. Pixels and voxels are stored in computer memory as a raster image or raster map, a two-dimensional or three-dimensional array of small integers transmitted or stored in an uncompressed or compressed form. Suitable digital image file formats include but are not limited to e.g., BMP, BPG, CD5, DEEP, ECW, Exif, FITS, FLIF, GIF, HDR, HEIF, ILBM, ILBM, IMG, IMG, JPEG 2000, JPEG XR, JPEG/JFIF, Layered Image File Format, Nrrd, PAM, PBM, PCX, PGF, PGM, PLBM, PNG, PNM, PPM, SGI, SID, Sun Raster, TGA, TIFF, VICAR, WEBP, and the like.

Digital images may be a variety of image bit depths depending, e.g., on the particular type of image captured (e.g., color or grayscale) and the sensitivity of the digital camera or other image capture device and may include but are not limited to e.g., 8-bit, 10-bit, 12-bit, 14-bit, 16-bit, 18-bit, 24-bit, 30-bit, 36-bit, 48-bit, 64-bit, and the like. In some instances, the channels of a color image may individually be or may be split into individual 8-bit grayscale images. In some instances, the channels of a color image may individually be or may be split into individual 16-bit grayscale images. In some instances, a digital color image may be generated from multiple individually captured grayscale images that are combined into a single image by assigning the individually captured grayscale images to different color channels of the single image. In other instances, all the colors of a digital color image are captures simultaneously, e.g., through the use of an image capture device having multiple photo detectors assigned to different colors and one or more optical devices for directing light of different colors to different photo detectors.

Digital images are captured by digital-image capture devices. A digital image capture device (i.e., digital imager) of the systems of the present disclosure, depending on the context, may acquire color or monochrome (e.g., grayscale) images. Acquired digital color or monochrome images may be captured using any suitable color or monochrome enabled image capturing device. Suitable digital color or monochrome image capturing devices will be stand-alone image capture units or may be an integrated image capturing device that is part of a larger integrated system including e.g., an integrated image and dispense system, etc. Suitable digital color or monochrome image capturing devices will vary greatly depending on the particular imaging context, the purposes of image capture and the associated components of the device or system as a whole.

At a minimum a suitable color or monochrome image capturing device, for use in the described methods, will include a digital color or monochrome camera capable of capturing a digital color or monochrome image and a means of storing the digital color or monochrome image and/or transferring the image to attached image processing circuitry or to an attached storage device for later transfer to image processing circuitry. Suitable digital color or monochrome cameras will vary and will generally include any digital color or monochrome camera with sufficiently high resolution and sufficient color or monochrome capture to capture an image that may be processed according to the methods described herein.

Depending on the particular features used in a subject methods or systems suitable digital cameras may include monochrome or color camera with resolution ranging from less than about 0.3 megapixel to about 14.0 megapixel or more including but not limited to e.g., 0.3 megapixel or more, 0.9 megapixel or more, 1.3 megapixel or more, 1.4 megapixel or more, 2 megapixel or more, 3 megapixel or more, 3.3 megapixel or more, 5 megapixel or more, 7 megapixel or more, 10 megapixel or more, 12 megapixel or more, 14.0 megapixel or more, and the like.

Suitable digital cameras include but are not limited to e.g., custom build digital cameras, consumer grade digital cameras (e.g., consumer grade digital cameras converted for microscopic use) and those digital microscopy cameras commercially available from various manufactures including but not limited to e.g., Dino-Eye, Dino-Lite, Jenoptik ProgRes, KoPa, Leica, Motic, Olympus, Omano, OptixCam, PixelLINK, Zeiss, etc.

In some instances, a digital camera of the instant system may be attached to a microscope configured for manual, automated or both manual and automated microscopy. Any suitable microscope may find use in the described systems provided the microscope is configured with sufficient optics and provides sufficient magnification to allow the capture of digital images that can be processed according to the methods described herein. As such, microscope components of the instant systems include custom units, e.g., as assembled from individual microscope components and commercially available units.

Suitable microscopes include but are not limited to e.g., those available from various manufactures including e.g., Bruker Optics (www(dot)brukeroptics(dot)com), Carl Zeiss (www(dot)zeiss(dot)com), CRAIC (www(dot)microspectra (dot)com), Edmund Optics (www(dot)edmundoptics(dot) com), FEI (www(dot)fei(dot)com), Hamamatsu (www(dot) hamamatsu(dot)com), Hirox-USA (www(dot)hirox-usa(dot) com), Hitachi High Technologies (www(dot)hitachi-hta (dot)com), JEOL (www(dot)jeol(dot)com), Keyence (www (dot)keyence(dot)com), Kramer (www(dot)kramerscientific (dot)com), Leica Microsystems (www(dot)leica(dot)com), Meiji Techno America (www(dot)meijitechno(dot)com), Motic Instruments (www(dot)motic(dot)com), Nikon Instruments (www(dot)nikoninstruments(dot)com), Ocean Optics (www(dot)oceanoptics(dot)com), Olympus (www (dot)olympusamerica(dot)com), OPTIKA Microscopes (www(dot)optikamicroscopes(dot)com), Phenom-World (www(dot)phenom-world(dot)com), Prior Scientific (www (dot)prior(dot)com), Warner (www(dot)warneronline(dot) com), and the like.

The imaging subsystems employed in the present disclosure may include stationary or movable components (e.g., stationary or movable imaging stage, stationary or movable objective lens, etc.). Moveable components may be computer controlled having one or more actuators or motors in electrical communication with a processor for moving the component(s) in accordance with signals or instructions received from the processor. Suitable imaging systems may include those having a stationary imaging stage and a moveable objective or objective turret, a stationary objective or objective turret and a moveable imaging stage, and the like. A non-limiting example of an integrated system having a stationary imaging stage and a moveable imaging subsystem is depicted in FIG. 2.

The systems of the present disclosure may include one or more backlash prevention devices. Moveable components of the subject systems may introduce vibration and/or error into the imaging subsystem thus, in some instances, complicating image capture and/or image processing due to "shaky" images. Such vibration and error may, in some instances, be due to backlash or "play" present in the movement driving components of the system (e.g., gears driving the moveable components of the imaging system). As such, one or more components of the system may include, within or attached the components, a backlash preventer that prevents and/or otherwise minimizes backlash in the system. Non-limiting examples of such backlash preventers include e.g., two gears connected with opposing springs. Gear backlash preventers may be incorporated into the drive components of the moveable aspects of systems described herein.

The herein described methods and systems may include storing digital information, including digital images and/or data extracted from digital images. Such digital information may be stored in any convenient manner including but not limited to storing the information in a computer memory and/or on one or more computer readable mediums. For example, digital images, processed or unprocessed, may be routed from an image capture device through a wired or wireless data connection to a computer memory or computer processor configured to write the data to computer memory or other computer readable medium. In some instances, data extracted from one or more digital images, processed or unprocessed, may be routed from an image capture device through a wired or wireless data connection to a computer memory or computer processor configured to write the data to computer memory or other computer readable medium.

Systems used in performing the herein described methods may include designated image processing circuitry, having instructions stored thereon or on an attached computer memory for performing one or more image processing functions or algorithms. Image processing circuitry may be, or may have an operable connection with additional circuitry, configured to perform one or more additional functions including but not limited to e.g., receive a digital image from an image capture device, retrieve a digital image from memory, retrieve a reference value from memory, store a processed image to memory, store a value obtained from a processed image to memory, store a result to memory, perform one or more cell counting and/or well identification functions, etc.

Cell Counting and Well Identification

The methods, devices, assemblages and systems of the present disclosure may include one or more cell counting and/or well identification steps. Such steps may be performed by cell counting software or cell counting computer applications available in various microscopy and/or image processing commercial and freely available software packages. "Cell counting", as used herein, will generally refer the process of identifying the number of cells present in a well or multiple wells of a multi-well device. "Well identification", as used herein, will generally refer to identifying whether a well of a multi-well device contains a predetermined desired number of cells. The desired number of cells of which a well may be identified may vary and may include e.g., the presence or absence of one or more cells, the presence of one cell, the presence of more than one cell (i.e., a multiplet), the presence of a particular multiplet (e.g., the presence of 2 cells, the presence of 3 cells, the presence of 4 cells, etc.), the absence of cells (i.e., an "empty" well), and the like. Accordingly, well identification may, in some instances, be binary, i.e., whether or not the well contains the desired number of cells.

In some embodiments, a cell counting software may be employed to count the number cells in each well. For example, CELLSELECT™ software (WAFERGEN (Wafer-Gen Bio-systems, Inc.)) may be used to count the cells, and determine which wells contain zero, one, two, or more cells. Cell counting may be performed, in some instances, on a generated composite image produced from multiple individual z-plane images. In certain embodiments, the software produces a table (e.g., filter file) that indicates all of the wells in the multi-well device that satisfy a criterion, such as selecting wells that contain a desired number of cells, such as a single cell. Single cells may be evaluated for or based on various criteria, e.g., being nucleated (e.g., as detected by Hoechst staining), having a membrane that is uncompromised or intact (e.g., as detected by Propidium Iodide), or other criteria and/or combinations thereof. Cell counting, e.g., as performed using cell counting software, may be employed to generate a map indicating which wells contain a desired number of cells and thus which wells are to be further processed. A map indicating which wells are to be further processed may include e.g., a dispensing map that indicates which wells are to receive one or more dispensed reagents for further processing.

In an exemplary embodiment, once particular wells are identified (e.g., those that contain a desired number of cells, including e.g., a single cell), the instrument may perform additional dispenses on the wells determined by a filter file, i.e., a table or map that indicates the wells in the multi-well device that satisfy a criterion, such as a desired number of cells.

In this embodiment, reagents are preloaded in a 384-well plate. With the imaging and dispensing capability integrated into an assembly, the multi-well device does not need to be moved or removed from the system (e.g., the multi-well device does not need to be moved or removed from a component locking it in place (e.g., on an imaging stage) close to the image and dispense assembly). In some instances, the multi-z approach may ensure that the cells are accounted with a high degree of accuracy. For example, in some instances, the accuracy may be sufficient such that the system may function without a centrifugation step that would require an operator to take the multi-well device out of the integrated instrument. The use of an integrated system does not preclude the centrifugation of the multi-well device, however, in certain embodiments. For example, in some instances, centrifugation may be employed prior to cell accounting for various reasons, including e.g., to increase the accuracy of cell accounting as compared to a similar process performed without centrifugation. Accordingly, in the methods described herein centrifugation may be optional or may be specifically excluded. In many embodiments, once cell counting, well identification and/or initial fluid dispenses are completed, the multi-well device is ready for additional processing such as thermal cycling, sample extraction, addition of exonucleases, library preparation, and/or eventually sequencing.

Applications

In certain embodiments, the methods, systems, and assemblies provided herein are employed with single-cell analysis in multi-well devices. Cell heterogeneity is a general feature of biological tissues and cells in general. Geneticists are striving to characterize complex diseases including cancer, autoimmune and neurological disorders. However, determining the underlying mechanisms driving these diseases remains elusive. As cells accumulate new mutations, they may form polyclonal cell populations that co-exist with normal cells. As a consequence, sequencing bulk cell populations can mask the underlying heterogeneity of these unique rare cell types, rendering it difficult to "find needles in the haystack." An alternate approach to reveal intra-population/inter-cell differences is to assess the nucleic acid sequences in selected individual cells from a population. Single-cell analyses have been used to define subpopulations with distinct DNA and RNA expression profiles. In summary, it is widely believed that single-cell analysis may uncover previously "hidden" mechanisms of complex disease.

A core requirement in the single-cell field is to clearly and unambiguously detect that the sample being assessed only contains a single cell. Traditional single cell isolation approaches including: FACS instrumentation, microfluidic capture, and limited or widely dispersed cell dilution methods are too expensive, labor intensive, require large sample input methods, and do not readily scale into the need for more cells within standard molecular biology workflows. On the other hand, random deposition of cells may be unpredictable/stochastically distributed, making predictions of cell distributions unwieldy.

An alternate approach, employed in embodiments of the present disclosure, is to dispense cells into reaction wells such that the average over many such dispenses results in a single cell being dispensed. A statistical description of this phenomenon is known as the Poisson distribution. In theory, dispensing a single cell per well (n=exactly 1 cell, but not 0, 2, 3, 4, 5, 6 etc. cells) is constrained by theta theoretical maxima=of 36.8% of wells will contain exactly 1 cell. However, the Poisson distribution can be leveraged to alter the input cell concentration to a very wide range of occupancy rates. A tradeoff in optimizing for a desired number of cells per well (i.e., 1 cell/well) exists. More specifically, optimizing to achieve a desired ratio (10:1 ratio where lambda approaches 0.185) of wells containing a single cell may result in an unsatisfactory percentage of wells without any cells (>82%). A similar approach attempting to specifically target 1 cell per well alongside a size separation approach has recently been reported. However, in that case, possibly due to the physical constraints in the cell capture device employed, only 10% of wells contained single cells. However, that methodology is complex and requires specialized reagents.

Emulsion-based methods, for selecting single cells include placing cells in water-in-oil emulsions. Such systems offer the advantage of insulating against cross contamination. However, these oil-separated compartments are difficult to manipulate. Moreover, such emulsions often require vortexing that depend on standard unselected Poisson statistics to achieve clonality. However, these approaches lead to only a small fraction of occupied and a large number of unoccupied compartments. As a consequence, emulsions are generated in microfluidic systems which increase cost and bear the significant disadvantage that once an emulsion is formed, it is difficult to exchange additional material in wells in a controlled fashion. Moreover, emulsion PCR is optionally performed using conditions that are not easily generalizable.

It is difficult to isolate single cells without expensive and complicated equipment. Moreover, such systems cannot typically capture more than 384 single cells. Provided herein are statistical methods combined with the combined dispensing and visualization, as well as cell visualization microscopy to visualize the cells in microfluidic chips (e.g., those sold by WAFERGEN (WaferGen Bio-systems, Inc.)). In certain embodiments, cells are diluted using Poisson statistics such that on average 1 cell per dispense volume is dispensed.

In certain embodiments, when wells are identified as having received zero cells, a second (and third) optional Recursive Poisson Distribution (RPD) step may be employed to circumvent the statistical limitations of the Poisson distribution, thereby raising single cell occupancy rates on-chip from a theoretical maxima of 37% to >50%. The RPD in this disclosure refers to the iterative cycle of, (a) dispensing cell-containing solutions into reaction vessels (wells, chambers, etc.) in a chip, (b) visualization of cells on-chip in individual wells, (c) identifying the on-chip cell counts (equal to zero, equal to one, and greater than one) in individual wells by software-aided microscopy, and, (d) performing additional dispense cycles of cell-containing solutions into individual wells specifically identified in the previous round as having a cell count of zero. The objective of RPD is to maximize the number of occupied reaction vessels (wells, chambers, etc.) containing a single-cell (or some other desired number of cells) above the theoretical limitations Poisson distribution for a single dispense. This disclosure does not place a limit on the number of iterative cycles.

In some embodiments, this disclosure describes methods of isolating individual cells and transferring them into individual wells of microfluidic wells (e.g., the wells of a SMARTCHIP™ multi-well device as sold by WAFERGEN (WaferGen Bio-systems, Inc.)). For example, in some embodiments, cells are first stained with the commonly available supravital dye Hoechst 33342 that emits a strong blue fluorescence when bound to DNA. The cells are counted, diluted to contain 1 cell per dispense volume, added to a source container (e.g. 384 well plate) and dispensed directly into a deep-well chip using a robotic micro-liquid dispenser (e.g., the Multiple Sample Nano Dispenser (MSND) as sold by WAFERGEN (WaferGen Bio-systems, Inc.)). Each well is then visualized by automated microscopy and image analysis to categorically confirm if either 0, 1, 2, 3 or 4 cells are dispensed in each well. This quality control step is both important and unique as it rapidly and definitively identifies the contents of wells in each of the wells in the chip.

The present disclosure is not limited by the type of cells that are employed. The present methods may include dispensing a volume of cell suspension into a well of a multi-well device. Essentially any cell suspension, containing any cells of any source, may be employed. Cells of interest may include a cell from any organism (e.g. a bacterial cell, an archaeal cell, a cell of a single-cell eukaryotic organism, a plant cell, an algal cell, a cell from a multicellular organism, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent (e.g., a mouse cell, a rat cell, etc.), a cell from a human, a cell from a non-human primate, etc.).

Any type of cell may be of interest (e.g. a pluripotent progenitor cell, a stem cell, e.g. an embryonic stem (ES) cell, an induced pluripotent stem (iPS) cell, a germ cell; a somatic cell (e.g., a somatic cell of mesodermal lineage, a somatic cell of endodermal lineage, a somatic cell of ectodermal lineage, e.g. a fibroblast, a hematopoietic cell, a neuron, a muscle cell, a bone cell, a hepatocyte, a pancreatic cell, an epithelial cell, etc.), a progenitor cell (e.g., a progenitor cell of mesodermal lineage, a progenitor cell of endodermal lineage, a progenitor cell of ectodermal lineage), a cell of an extraembryonic lineage; an in vitro or in vivo embryonic cell of an embryo at any stage, e.g., a 1-cell, 2-cell, 4-cell, 8-cell, etc. stage (e.g., a nematode embryo, a fly embryo, a xenopus embryo, a zebrafish embryo, a mouse embryo; a rat embryo, a non-human primate embryo, etc.), immune cells (e.g., primary or progenitor derived immune cells such as e.g., lymphocytes (T cells (immune cells expressing CD3 including T-helper cells (CD4+ cells), cytotoxic T-cells (CD8+ cells), T-regulatory cells (Treg) and gamma-delta T cells), B cells, natural killer (NK) cells) and myeloid-derived cells (neutrophil, eosinophil, basophil, monocyte, macrophage, dendritic cells)), and the like. Also of interest are modified cells such as e.g., genetically modified cells, including but not limited to e.g., genetically modified stem cells, genetically modified immune cells (e.g., engineered immune cells such as those employed in: antibody production/screening, engineered immune receptor (e.g., TCR) production/screening, adoptive immunotherapies (e.g., chimeric antigen receptor expressing immune cells), etc.) and the like.

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Primary cells, in many instances, are not cultured and may, e.g., be utilized in a method of the present disclosure following isolation and/or dissociation directly, i.e., without undergoing cell culture.

Primary cells may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc., are conveniently harvested by biopsy. An appropriate solution may be used for dispersion, dissociation and/or suspension of harvested cells. Such solution may be a balanced salt solution, e.g. normal saline, phosphate-buffered saline (PBS), Hank's balanced salt solution, etc., with or without supplementation with serum (e.g., fetal calf serum) or other naturally occurring factors, in conjunction with an acceptable buffer at low concentration (e.g., from 5-25 mM). Convenient buffers include HEPES, phosphate buffers, lactate buffers, etc. Cells may be used immediately, or they may be stored, frozen, for some period of time, being thawed and capable of being reused. In such cases, the cells may be frozen in a freezing medium, including e.g., 10% DMSO, 50% serum, 40% buffered medium, or some other such solution as is commonly used in the art to preserve cells at such freezing temperatures, and thawed in any convenient manner for thawing frozen cells.

In some instances, cells of interest may include pluripotent progenitor cells. The terms "pluripotent progenitor cells", "pluripotent progenitors", "pluripotent stem cells", "multipotent progenitor cells" and the like, as used herein refer to cells that are capable of differentiating into two or more different cell types and proliferating. Non limiting examples of pluripotent precursor cells include but are not limited to embryonic stem cells, blastocyst derived stem cells, fetal stem cells, induced pluripotent stem cells, ectodermal derived stem cells, endodermal derived stem cells, mesodermal derived stem cells, neural crest cells, amniotic stem cells, cord blood stem cells, adult or somatic stem cells, neural stem cells, bone marrow stem cells, bone marrow stromal stem cells, hematopoietic stem cells, lymphoid progenitor cells, myeloid progenitor cells, mesenchymal stem cells, epithelial stem cells, adipose derived stem cells, skeletal muscle stem cells, muscle satellite cells, side population cells, intestinal stem cells, pancreatic stem cells, liver stem cells, hepatocyte stem cells, endothelial progenitor cells, hemangioblasts, gonadal stem cells, germline stem cells, and the like. Pluripotent progenitor cells may be acquired from public or commercial sources or may be newly derived.

In certain embodiments, cancer cells, circulating cancer cells, stem cells, and cancer stem cells are employed. The term "cancer cells" may include primary cancer cells (i.e., cancer cells derived from a primary source such as e.g., a cancer or tumor biopsy) as well as cultured cancer cells (i.e., cancer cell lines, including e.g., immortalized cancer cell lines such as e.g., 3T3 cells, A549 cells, F11 cells, HeLa cells, HEK 293 cells, Jurkat cells, Vero cells, and the like). Cancer cells of interest include primary cancer cells isolated from a cancer (e.g., a carcinoma, a sarcoma, a myeloma, a leukemia, a lymphoma, a cancer of mixed cell types) from an individual, including but not limited to e.g., cancer cells isolated from any of the following cancers: Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, ect.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sézary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenström Macroglobulinemia and Wilms Tumor.

Most cancer deaths appear to be caused by metastatic spread and growth by circulating tumor cells at distant organs. Circulating tumor cells (CTCs), CTC clusters (two or more individual CTCs bound together), and cancer stem cells (CSCs) may be initially localized, latent systemic, or post-adjuvant treatment depleted. Consequently, CTCs and the relevant stem cells are frequently present at low numbers within a large background of normal non-cancerous cells. The low frequency of these cells generates a complex "needle in a haystack" analysis problem for detecting the required cancer cell signal within the large 'noise" background. Detection of cancer cell specific cell surface markers and analysis of these cells is deeply relevant to understanding the biology of metastatic spread. The methods and systems provided herein allow isolation and analysis of such important cancer cells.

Single-cell, multiple-cell and cell clusters may initially be either enriched or depleted from a cell or tissue milieu or population, based on the presence of antigenic/phenotypic cell-surface or intra-cellular markers including but not restricted to: protein, lipid, carbohydrate (i.e. glycosylation) post-translational modifications of those moieties, nucleic acids and their modifications, or varying combinations of these moieties. Detection of cell surface markers in single cells—including cancer cells—and transferring those cells into discrete individual wells of a multi-well device (e.g., wells of a SMARTCHIP™ as sold by WAFERGEN (Wafer-Gen Bio-systems, Inc.)) may be performed with the methods and systems described herein. In other embodiments, labelled cells may be dispensed directly into wells and antigenic moieties detected directly in chip via standard or automated microscopy using a variety of widely available fluorescence filters.

Any convenient methods of cell labeling and/or detection may be employed. For example, in some instances, cellular markers (including intracellular markers and cell surface markers) may be bound by a specific binding member that is detectable. Detectable specific binding members may be directly detectable (e.g., coupled to a detectable moiety, such as e.g., a fluorescent molecule) or may be indirectly detectable (e.g., coupled to a binding site (e.g., a biotin, a streptavidin, an immunoglobulin domain, an affinity tag, etc.) bound by a second specific binding member that is detectable (e.g., fluorescent secondary antibody). Specific binding members also include nucleic acids including but not limited to e.g., aptamers, oligonucleotide probes (e.g., RNA probes, DNA probes, LNA probes, etc.) that bind or hybridize with a specific target (e.g., a protein or nucleic acid target). Nucleic acid specific binding members may be directly detectable (e.g., conjugated to a fluorophore) or indirectly detectable (e.g., through binding of a second specific binding member).

Labeling of cells may be performed on live cells (e.g., through binding a specific binding member to a cell surface marker) or fixed cells, where permeabilization may or may not be employed depending on whether a subject marker is accessible on the surface or the cell or intracellular. Useful methods of labeling include immunohistochemistry, in situ hybridization, and the like. In some instances, cells may be labeled with an expressed detectable molecule such as e.g., an expressed fluorescent protein, an expressed bioluminescent protein, and the like. Where fixed and/or permeabilized cells are employed any convenient method of fixing and/or permeabilizing may be employed including cross-linking and non-crosslinking fixatives including but not limited to e.g., formaldehyde, paraformaldehyde, formaldehyde/acetone, methanol/acetone, ethanol, methanol, Carnoy's, and the like. Permeabilization may be facilitated by any convenient method including e.g., one or more chemical or enzymatic methods including e.g., protease digestion, mild detergent exposure (e.g., Triton X-100, NP-40, saponin, etc.). In some instances, cells may be unfixed.

In some instances, cells may be labeled with one or more nucleic acid or cytoplasm dyes and/or viability dyes including but not limited to e.g., DNA dyes, DNA intercalating dyes, vital dyes, propidium iodide, calcein, Hoechst dyes, etc. Non-limiting examples of viability dyes, for detecting live and/or dead cells, include e.g., propidium iodide (PI), 7-amino-actinomycin D (7-AAD), and those available from commercial distributors such as Fixable Viability Dye eFluor 455UV/450/506/520/660/780 (Affymetrix eBioscience, San Diego, Calif.), LIVE/DEAD Fixable Blue/Violet/Aqua/Yellow stain (Life Technologies, Grand Island, N.Y.), Zombie Aqua/Green/NIR/RED/UV/Violet/Yellow (BioLegend, San Diego, Calif.), and the like. Non-limiting examples of nucleic acid dyes include e.g., Hoechst 33342 (2'-(4-Ethoxyphenyl)-5-(4-methyl-1-piperazinyl)-1H,1'H-2,5'-bibenzimidazole trihydrochloride) and Hoechst 33258 (4-[6-(4-Methyl-1-piperazinyl)-1',3'-dihydro-1H,2'H-2,5'-bibenzimidazol-2'-ylidene]-2,5-cyclohexadien-1-one trihydrochloride) and others of the Hoechst series; SYTO 40, SYTO 11, 12, 13, 14, 15, 16, 20, 21, 22, 23, 24, 25 (green); SYTO 17, 59 (red), DAPI, DRAQ5™ (an anthraquinone dye with high affinity for double stranded DNA), YOYO-1, propidium iodide, YO-PRO-3, TO-PRO-3, YOYO-3 and TOTO-3, SYTOX Green, SYTOX, methyl green, acridine homodimer, 7-aminoactinomycin D, 9-amino-6-chloro-2-methoxyacridine, and the like.

As a non-limiting example, methods of circulating tumor cell (CTC) enrichment and visualization are known in the art and may be employed for generating (and later visualizing) an initial cell suspension that may be employed in the methods and systems described herein. For example, Table 1 of Krebs et al. Nat Rev Clin Oncol. 2014 March; 11(3): 129-44 (herein incorporated by reference, and specifically with respect to Table 1). Examples of markers that can be employed to enrich and visualize CTCs include, but are not limited to: CD45, EpCAM, MUC1, and HER2. Antibodies to such markers may be employed to label and visualize such cells. Any type of suitable method may be employed for isolating and enriching CTCs, such as flow cytometry, column binding, etc.

In some instances, the sample from which cells are derived may be a biopsy or swab, e.g., a biopsy or swab collected to diagnose, monitor, or otherwise evaluate a subject, e.g., diagnose the subject for a cellular deficiency or disease, e.g., cancer. In some instances, a sample from which the cells are derived may be a previously collected and stored sample, e.g., a banked tissue sample, from the subject to be treated, including but not limited to e.g., stored cardiac tissue or cells, stored musculoskeletal tissue or cells, stored reproductive tissue or cells, stored skin tissue or cells, stored bone tissue or cells, stored bone marrow tissue or cells, stored vascular tissue or cells, stored umbilical cord blood tissue or cells, and the like. In some instances, a sample from which the cells are derived is fresh, i.e., not previously stored or frozen.

Following the collection of a cell or tissue or organ sample or biopsy or swab the cells may be processed. For example, in the case of solid and/or semi-solid tissues (e.g., solid tumors, skin tissue, brain tissue, muscle tissue, liver tissue, adipose tissue, etc.) the tissue may be dissociated into a single cell suspension. Any convenient method of cell dissociation may be employed including e.g., enzymatic (e.g., protease) dissociation, non-enzymatic (e.g., chemical or physical) dissociation, and the like. The cells of a dissociated solid or semi-solid tissue sample may be further processed, including e.g., through fractionation, enrichment, sorting, staining, etc., or may not be further processed. Cells of liquid cellular samples (e.g., blood, amniotic fluid, etc.) may be processed, including e.g., through fractionation, enrichment, sorting, staining, etc., or may not be processed. Any convenient technique or device may be employed to facilitate such processing steps including but not limited to e.g., density gradients, centrifuges, tissue culture dishes/flasks, filters, syringes, blood separation tubes, FACS, and the like.

Prepared cell suspensions, whether or not involving dissociation and/or one or more processing steps (e.g., as described above), may be prepared in or transferred to a suitable container for cell dispensing. Suitable containers for cell dispensing may be referred to herein as "source containers" or "source devices" which may have one or more "source compartments" or "source device wells". Suitable source containers include but are not limited to e.g., tubes, flasks, dishes, bottles, troughs, multi-well devices (e.g., multi-well plates, including e.g., 6-, 12-, 24-, 36-, 48-, 96-, 384- and 1536-well plates, and the like). In some instances, a subject source container may be configured such that the dispense tip may contact cell suspension present in the source container, e.g., for extracting cell suspension from the source container. In some instances, a source container may be connected, e.g., by a tube or other liquid transfer device, to the dispenser to facilitate filling of the dispense tip, e.g., by back-filling the dispense tip. Configurations of source containers may vary and may include where the source container and the dispense tip are configured to be compatible.

The present disclosure is not limited by the type of multi-well testing devices (e.g., plates or chips) employed. In general, such devices have a plurality of wells that contain, or are dimensioned to contain, liquid (e.g., liquid that is trapped in the wells such that gravity alone cannot make the liquid flow out of the wells). One exemplary chip is the 5184-well SMARTCHIP™ multi-well device sold by WAFERGEN (WaferGen Bio-systems, Inc.). Other exemplary chips are provided in U.S. Pat. Nos. 8,252,581; 7,833,709; and 7,547,556, all of which are herein incorporated by reference in their entireties including, for example, for the teaching of chips, wells, thermocycling conditions, and associated reagents used therein). Other exemplary chips include the OPENARRAY™ plates used in the QUANTSTUDIO™ real-time PCR system (sold by Thermo Fisher Scientific Inc.). Another exemplary multi-well device is a 96-well or 384-well plate.

The overall size of the multi-well devices may vary and it can range, for example, from a few microns to a few centimeters in thickness, and from a few millimeters to 50 centimeters in width or length. In some instances, the size of the entire device ranges from about 10 mm to about 200 mm in width and/or length, and about 1 mm to about 10 mm in thickness. In some embodiments, the chip is about 40 mm in width by 40 mm in length by 3 mm in thickness.

The total number of wells (e.g., nanowells) on the multi-well device may vary depending on the particular application in which the subject chips are to be employed. The density of the wells on the chip surface may vary depending on the particular application. The density of wells, and the size and volume of wells, may vary depending on the desired application and such factors as, for example, the species of the organism for which the methods of this disclosure are to be employed.

The present disclosure is not limited by the number of wells in the multi-well device or the number of wells in the multi-well source device. A large number of wells may be incorporated into a device. In various embodiments, the total number of wells on the device is from about 100 to about 200,000, or from about 5000 to about 10,000. In other embodiments the device comprises smaller chips, each of which comprises about 5,000 to about 20,000 wells. For example, a square chip may comprise 125 by 125 nanowells, with a diameter of 0.1 mm.

Useful source devices, i.e., devices configured to contain the source fluid (e.g., cell suspension) for dispensing, will vary and may include single vessel devices as well as multi-well devices. For example, in some instances, a subject source device may include a single well, trough, tube, bottle, flask, dish, bowl, etc. configured to contain the source liquid for transfer into a dispenser. In some instances, a subject source device may include a plurality of wells or arrayed tubes configured to contain the source liquid for transfer into a dispenser. Source devices may be specifically configured to align with dispensers having one or multiple dispense tips. For example, a multi-well source device may include wells that are spaced to correspond with the spacing between the dispenser tips of a multi-tip dispenser such that more than one, including all, of the dispenser tips may be each simultaneously inserted into a well of the multi-well source device. Multi-well source devices may thus be configured to be compatible with the dispense tips of multi-tip dispensers, including where the multi-well source device has a number of wells equal to the number of dispenser tips or where the number of wells and the number of dispenser tips are unequal.

The wells (e.g., nanowells) in the multi-well devices may be fabricated in any convenient size, shape or volume. The well may be about 100 µm to about 1 mm in length, about 100 µm to about 1 mm in width, and about 100 µm to about 1 mm in depth. The length, width (or diameter) and height of the wells may vary and may range from less than 50 µm to more than 5 mm, including but not limited to e.g., 50 µm to 5 mm, 75 µm to 5 mm, 100 µm to 5 mm, 200 µm to 5 mm, 300 µm to 5 mm, 400 µm to 5 mm, 500 µm to 5 mm, 600 µm to 5 mm, 700 µm to 5 mm, 800 µm to 5 mm, 900 µm to 5 mm, 1 mm to 5 mm, 2 mm to 5 mm, 3 mm to 5 mm, 4 mm to 5 mm, 50 µm to 2 mm, 75 µm to 2 mm, 100 µm to 2 mm, 200 µm to 2 mm, 300 µm to 2 mm, 400 µm to 2 mm, 500 µm to 2 mm, 600 µm to 2 mm, 700 µm to 2 mm, 800 µm to 2 mm, 900 µm to 2 mm, 1 mm to 2 mm, 50 µm to 1 mm, 75 µm to 1 mm, 100 µm to 1 mm, 200 µm to 1 mm, 300 µm to 1 mm, 400 µm to 1 mm, 500 µm to 1 mm, 50 µm to 500 mm, 75 µm to 500 mm, 100 µm to 500 mm, 200 µm to 500 mm, 300 µm to 500 mm, 400 µm to 500 mm, etc. In various embodiments, each nanowell has an aspect ratio (ratio of depth to width) of from about 1 to about 4, including e.g., 1 to 4, 1 to 3, 1 to 2, 1, 2 to 4, 2 to 3, 2, 3 to 4, 3, and 4. In some embodiments, each nanowell has an aspect ratio of about 2. The transverse sectional area may be circular, elliptical, oval, conical, rectangular, triangular, polyhedral, or in any other shape. The transverse area at any given depth of the well may also vary in size and shape.

In some embodiments, the wells have a volume of from about 0.1 nl to about 1 µl. A nanowell may have a volume of less than 1 µl, in some instances less than 500 nl. The volume may be less than 200 nl, or less than 100 nl. In some embodiments, the volume of the nanowell is about 100 nl. In some embodiments, the volume of the nanowell is about 150 nl. The volume of a well of a multi-well device may vary and may range from less than 0.1 nl to 100 µl or more, including but not limited to e.g 0.1 nl to 100 µl, 0.1 nl to 90 µl, 0.1 nl to 80 µl, 0.1 nl to 70 µl, 0.1 nl to 60 µl, 0.1 nl to 50 µl, 0.1 nl to 40 µl, 0.1 nl to 30 µl, 0.1 nl to 20 µl, 0.1 nl to 15 µl, 0.1 nl to 10 µl, 0.1 nl to 5 µl, 0.1 nl to 1 µl, 0.1 nl to 900 µl, 0.1 nl to 800 µl, 0.1 nl to 700 µl, 0.1 nl to 600 µl, 0.1 nl to 500 µl, 0.1 nl to 450 µl, 0.1 nl to 400 µl, 0.1 nl to 350 µl, 0.1 nl to 300 µl, 0.1 nl to 250 µl, 0.1 nl to 200 µl, 0.1 nl to 150

μl, 0.1 nl to 100 μl, 0.1 nl to 50 μl, etc. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments. In some instances, a well of high inner surface to volume ratio may be coated with materials to reduce the possibility that the reactants contained therein may interact with the inner surfaces of the well if this is desired. Coating is particularly useful if the reagents are prone to interact or adhere to the inner surfaces undesirably. Depending on the properties of the reactants, hydrophobic or hydrophilic coatings may be selected. In some instances, the subject methods and systems may employ a multi-well device having a relatively hydrophobic top surface and/or relatively hydrophilic wells, e.g., as described in PCT Application No. US2017/034568, the disclosure of which is incorporated herein by reference in its entirety. A variety of appropriate coating materials are available in the art. Some of the materials may covalently adhere to the surface, others may attach to the surface via non-covalent interactions. Non-limiting examples of coating materials include silanization reagent such as dimethychlorosilane, dimethydichlorosilane, hexamethyldisilazane or trimethylchlorosilane, polymaleimide, and siliconizing reagents such as silicon oxide, AQUASIL™ and SURFA-SIL™ (sold by Thermo Fisher Scientific Inc.). Additional suitable coating materials are blocking agents such as amino acids, or polymers including but not limited to polyvinylpyrrolidone, polyadenylic acid and polymaleimide. Certain coating materials can be cross-linked to the surface via heating, radiation, and by chemical reactions. Those skilled in the art will know of other suitable means for coating a nanowell of a multi-well device, or will be able to ascertain such, without undue experimentation.

An exemplary multi-well device (e.g., chip) may have a thickness of about 0.625 mm, with a well have having dimensions of about 0.25 mm (250 μm) in length and width. The nanowell depth can be about 0.525 mm (525 μm), leaving about 0.1 mm of the chip beneath a given well. A nanowell opening can include any shape, such as round, square, rectangle or any other desired geometric shape. By way of example, a nanowell can include a diameter or width of between about 100 μm and about 1 mm, a pitch or length of between about 150 μm and about 1 mm and a depth of between about 10 μm to about 1 mm. The cavity of each well may take a variety of configurations. For instance, the cavity within a nanowell may be divided by linear or curved walls to form separate but adjacent compartments.

The wells (e.g., nanowells) of the multi-well device may be formed using, for example, commonly known photolithography techniques. The nanowells may be formed using a wet KOH etching technique, an anisotropic dry etching technique, mechanical drilling, injection molding and or thermo forming (e.g., hot embossing).

Reagents may be pre-dispensed into the wells of a multi-well device, or added after a cell or cells are added to a well, or both. Reagents contained within the liquid in the multi-well device (whether added before, during or after cell dispensing) depend on the reaction that is to be run with the single cell (or multiple cells) that is deposited into each well. In some embodiments, the wells contain a reagent for conducting the nucleic acid amplification reaction. Reagents can be reagents for immunoassays, immunoassays, nucleic acid preparation, analysis and detection assays (including but not limited to nucleic acid amplification, e.g., PCR (including e.g., sequence specific PCR, random primed PCR, qPCR, multiplex PCR, etc.), whole genome amplification (WGA), library preparation, reverse transcription, cDNA preparation, template switching, tagmentation, Next Generation Sequencing (NGS), library preparation (e.g., for NGS) and the like. Reagents can be in a dry state or a liquid state in a unit of the chip.

Non-limiting examples of reagents that may be added to and/or already present in a well of a multi-well device include but are not limited to e.g., oligonucleotides (including e.g., primers and probes, including DNA, RNA and nucleotide analog oligonucleotide primers and probes, template switch oligonucleotides, etc.), barcode containing nucleic acids, sequencing adapter containing nucleic acids, template nucleic acids (e.g., DNA templates, RNA templates, etc.), transposon nucleic acids, enzymes (e.g., polymerases (e.g., reverse transcriptase, RNA polymerase, etc.), transposases, nucleases (e.g., endonucleases (e.g., restriction endonucleases), exonucleases, Cas9 nucleases, etc.), ligases, DNA repair enzymes (e.g., uracil-DNA glycosylase, endonuclease III, IV, V, VIII, etc.), methyltransferases, phosphatases, sulfurylases, recombinases, kinases, nuclease inhibitors (e.g., an RNase inhibitor), etc.), dNTPs (e.g., dATP, dCTP, dGTP, dTTP, and/or dUTP), dyes (e.g., DNA binding dye (e.g., DAPI, Hoechst, SYBR® Green, etc.), viability dyes, etc.), salts, metal cofactors, enzyme-stabilizing components (e.g., DTT), and the like.

In some embodiments, the wells contain at least one of the following reagents: a probe, a polymerase, and dNTPs. In other embodiments, the wells contain a solution comprising a probe, a primer and a polymerase. In various embodiments, each well comprises (1) a primer for a polynucleotide target within said standard genome, and (2) a probe associated with said primer which emits a concentration dependent signal if the primer binds with said target. In various embodiments, each well comprises a primer for a polynucleotide target within a genome, and a probe associated with the primer which emits a concentration dependent signal if the primer binds with the target. In another embodiment, at least one well of the chip contains a solution that comprises a forward PCR primer, a reverse PCR primer, and at least one FAM labeled MGB quenched PCR probe. In some embodiments, primer pairs are dispensed into a well and then dried, such as by freezing. The user can then selectively dispense, such as nano-dispense, the sample, probe and/or polymerase.

In other embodiments of the disclosure, the wells may contain any of the above solutions in a dried (e.g., lyophilized) form. In this embodiment, this dried form may be coated to the wells or be directed to the bottom of the well. The user can add a mixture of water and the captured cells to each of the wells before analysis. In these embodiments, the chip comprising the dried down reaction mixture may be sealed with a liner, stored or shipped to another location.

Multi-well devices, with a single cell in each well, may be used for genotyping, gene expression, or other DNA assays performed by PCR. Assays performed in the plate are not limited to DNA assays such as TAQMAN, TAQMAN Gold, SYBR gold, and SYBR green but also include other assays such as receptor binding, enzyme, and other high throughput screening assays.

In some embodiments cells are subjected (e.g., after lysis and/or other processing steps) to amplification and/or sequencing analysis. Conducting one or more amplification reactions may comprise one or more PCR-based amplifications, non-PCR based amplifications, or a combination thereof. Illustrative non-limiting examples of nucleic acid amplification techniques include, but are not limited to, polymerase chain reaction (PCR), reverse transcription polymerase chain reaction (RT-PCR), nested PCR, linear amplification, multiple displacement amplification (MDA), real-time SDA, rolling circle amplification, circle-to-circle amplification transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to permit exponential increase in copy numbers of target nucleic acids. In a variation called RT-PCR, reverse transcriptase (RT) is used to make a complementary DNA (cDNA) from RNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemi-phosphorothioated primer extension product, endonuclease-mediated nicking of a hemi-modified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

In some embodiments, nucleic acid sequencing methods are utilized (e.g., for detection of amplified nucleic acids). In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306, 597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485, 944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330;

herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specific color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In some embodiments, the technology finds use in Heli-Scope by Helicos BioSciences (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

In some embodiments, the Ion Torrent technology is employed. The Ion Torrent technology is a method of DNA sequencing based on the detection of hydrogen ions that are released during the polymerization of DNA (see, e.g., *Science* 327(5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics is used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other single molecule sequencing methods include realtime sequencing by synthesis using a VisiGen platform (Voelkerding et al., *Clinical Chem.*, 55: 641-58, 2009; U.S. Pat. No. 7,329,492; U.S. patent application Ser. No. 11/671, 956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Reagents for any suitable type of assay may be added to the wells of the multi-well chip (e.g., using a multi-well dispenser, such as those sold by WAFERGEN (WaferGen Bio-systems, Inc.)). Such reagents may be added to the wells before or after a cell (e.g., a single cell) is added to a well. In certain embodiments, protein detection assay components (e.g., anti-body based assays) are added to the wells. In other embodiments, SNP detection assay components are added to the wells. In other embodiments, nucleic acid sequencing assay components are added to the wells. In certain embodiments, nucleic acid sequence assay components that employ barcoding for labelling individual mRNA molecules, and/or for labeling for cell/well source (e.g., if wells pooled before sequencing analysis), and/or for labeling particular multi-well chips (e.g., if wells from two or more multi-well chips are pooled prior to sequencing) are employed. Examples of such barcoding methodologies and reagents are found in Pat. Pub. US2007/0020640, Pat. Pub. 2012/0010091, U.S. Pat. Nos. 8,835,358, 8,481,292, Qiu et al. (Plant. Physiol., 133, 475-481, 2003), Parameswaran et al. (Nucleic Acids Res. 2007 October; 35(19): e130), Craig et al. reference (Nat. Methods, 2008, October, 5(10):887-893), Bontoux et al. (Lab Chip, 2008, 8:443-450), Esumi et al. (Neuro. Res., 2008, 60:439-451), Hug et al., J. Theor., Biol., 2003, 221: 615-624), Sutcliffe et al. (PNAS, 97(5):1976-1981; 2000), Hollas and Schuler (Lecture Notes in Computer Science Volume 2812, 2003, pp 55-62), and WO201420127; all of which are herein incorporated by reference in their entireties, including for reaction conditions and reagents related to barcoding and sequencing of nucleic acids.

In some embodiments, the barcode tagging and sequencing methods of WO2014201272 ("SCRB-seq" method) are employed. The necessary reagents for the SCRB-seq method (e.g., modified as necessary for small volumes) are added to the wells of the multi-well chips (e.g., where the single cell in the well has been lysed). Briefly, the SCRB-seq method amplifies an initial mRNA sample from a single cell in multi-well plates (as described above), where each well has a single cell. Initial cDNA synthesis uses a first primer with: i) N6 or N11 for cell/well identification, ii) N10 for particular molecule identification, iii) a poly T stretch to bind mRNA, and iv) a region that creates a region where a second template-switching primer will hybridize. The second primer is a template switching primer with a poly G 3' end, and 5' end that has iso-bases. After cDNA amplification, the tagged cDNA single cell/well samples are pooled. Then full-length cDNA synthesis occurs with two different primers, and full-length cDNA is purified. Next, a NEXTERA sequencing library is prepared using an i7 primer (adds one of 12 i7 tags to identify particular multi-well plates) and P5NEXTPT5 to add P5 tag for NEXTERA sequencing (P7 tag added to other end for NEXTERA). The library is purified on a gel, and then NEXTERA sequencing occurs. As a non-liming example, with twelve i7 plate tags, and 384 cell/well-specific barcodes, this allows total of 4,608 single cell transcriptomes to be done at once. This method allows for quantification of mRNA transcripts in single cells and allows users to count the absolute number of transcript molecules/cell to remove any variables from normalization.

In further embodiments, image and chip mapped wells within the chip are dynamically and/or statically selected for further analysis by a combination of single or multiple addition of reagents for detection and/or resolution of nucleic acids or lipids or carbohydrates or protein cell components reagents.

Computer Related Embodiments

As summarized above, components, e.g., dispenser components and components thereof, imaging components and components thereof, etc., of the subject systems and employed in the subject methods may be computer controlled (i.e., robotic). Accordingly, the subject methods and systems may employ a processor connected to or otherwise in communication with one or more electrical components of the system to control one or more actions of the components.

In some instances, the image processing circuitry is specifically configured or programed to perform the functions according to the methods as described herein, including image processing functions, composite image generating functions, multi-well device map generating functions, etc., and may include at least one data processing unit for performing data related functions.

By "data processing unit", as used herein, is meant any hardware and/or software combination that will perform the functions required of it. For example, any data processing unit herein may be a programmable digital microprocessor such as available in the form of an electronic controller, mainframe, server or personal computer (desktop or portable). Where the data processing unit is programmable, suitable programming can be communicated from a remote location to the data processing unit, or previously saved in a computer program product (such as a portable or fixed computer readable storage medium, whether magnetic, optical or solid state device based).

In some instances, the components of the systems as described herein may be connected by a wired data connection. Any suitable and appropriate wired data connection may find use in connecting the components of the described systems, e.g., as described herein, including but not limited to e.g., commercially available cables such as a USB cable, a coaxial cable, a serial cable, a C2G or Cat2 cable, a Cat5/Cat5e/Cat6/Cat6a cable, a Token Ring Cable (Cat4), a VGA cable, a HDMI cable, a RCA cable, an optical fiber cable, and the like. In some instances, wireless data connections may be employed including but not limited to e.g., radio frequency connections (e.g., PAN/LAN/MAN/WAN wireless networking, UHF radio connections, etc.), an infrared data transmission connection, wireless optical data connections, and the like.

As summarized above, the devices and systems of the instant disclosure may further include a "memory" that is capable of storing information such that it is accessible and retrievable at a later date by a computer. Any desired information may be stored on such a memory, including but not limited to e.g., instructions for performing one or more steps of a method, and the like. Any convenient data storage structure may be chosen, based on the means used to access the stored information. In certain aspects, the information may be stored in a "permanent memory" (i.e., a memory that is not erased by termination of the electrical supply to a computer or processor) or "non-permanent memory". Computer hard-drive, CD-ROM, floppy disk, portable flash drive and DVD are all examples of permanent memory. Random Access Memory (RAM) is an example of non-permanent memory. A file in permanent memory may be editable and re-writable.

Substantially any circuitry can be configured to a functional arrangement within the devices and systems for performing the methods disclosed herein. The hardware architecture of such circuitry, including e.g., a specifically configured computer, is well known by a person skilled in the art, and can comprise hardware components including one or more processors (CPU), a random-access memory (RAM), a read-only memory (ROM), an internal or external data storage medium (e.g., hard disk drive). Such circuitry can also comprise one or more graphic boards for processing and outputting graphical information to display means. The above components can be suitably interconnected via a bus within the circuitry, e.g., inside a specific-use computer. The circuitry can further comprise suitable user interfaces for communicating with general-purpose external components such as a monitor, keyboard, mouse, network, etc. In some embodiments, the circuitry can be capable of parallel processing or can be part of a network configured for parallel or distributive computing to increase the processing power for the present methods and programs. In some embodiments, the program code read out from the storage medium can be written into a memory provided in an expanded board inserted in the circuitry, or an expanded unit connected to the circuitry, and a CPU or the like provided in the expanded board or expanded unit can actually perform a part or all of the operations according to the instructions of the programming, so as to accomplish the functions described.

The instant disclosure includes computer readable medium, including non-transitory computer readable medium, which stores instructions for methods, or portions thereof, described herein. Aspects of the instant disclosure include computer readable medium storing instructions that, when executed by a computing device, cause the computing device to perform one or more steps of a method as described herein.

In certain embodiments, instructions in accordance with the methods described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

The following examples are offers by way of illustration and not by way of limitation.

EXAMPLES

Example 1: Influence of Centrifugation, z-Plane Sampling and Cell Dispense Volume on Identification of Candidate Wells The influence of centrifugation on the number of identified candidate wells was investigated. Specifically, cell suspension was Poisson dispensed into 1 mm (150 nl) and 1.6 mm (250 nl) multi-well chips and candidate well identification (i.e., the identification of wells having the desired number of cells, in this case "one") was performed with before and after centrifugation of the multi-well chips. Using imaging at three z-focal planes (Z1 to Z3) pre- and post-centrifugation, the resulting number of candidate wells was quantified. Tables 2 and 3 provide the results of this quantification for the 1 mm and 1.6 mm chips, respectively, and include control candidate well quantification results generated using an Olympus microscope.

TABLE 2

1 mm (150 nl) Regular Chip

| Imaging condition | Candidates (Z1 to Z3 only for V2) |
| --- | --- |
| V2 imaging - Pre centrifuge | 950 |
| V2 imaging - Post centrifuge | 1187 |
| Olympus | 1350 |

TABLE 3

1.6 mm (250 nl) Deep Chip

| Imaging condition | Candidates (Z1 to Z3 only for V2) |
| --- | --- |
| V2 imaging - Pre centrifuge | 968 |
| V2 imaging - Post centrifuge | 1259 |
| Olympus | 1427 |

The influence of z-plane sampling on the number of identified candidate wells, with and without centrifugation, was also investigated. Candidate well identification was performed on the 1 mm (150 nl) chip at various levels of z-plane sampling, before or after centrifugation. Specifically, sampling was performed using one (Z1), two (Z1+Z2), three (Z1+Z2+Z3), four (Z1+Z2+Z3+Z4) or five (Z1+Z2+Z3+Z4+Z5) focal planes in the z-axis of the chip. Results for the candidate well quantification at the various sampling levels are provided in Table 4.

TABLE 4

1 mm (150 nl) Regular Chip

| Focal Planes in Z-axis | Post Centrifugation | Pre Centrifugation |
| --- | --- | --- |
| Z1 | 1219 | 952 |
| Z1 + Z2 | 1129 | 919 |
| Z1 + Z2 + Z3 | 1187 | 950 |
| Z1 + Z2 + Z3 + Z4 | 1198 | 966 |
| Z1 + Z2 + Z3 + Z4 + Z5 | 1199 | 976 |

The influence of z-plane sampling on the number of identified candidate wells was further evaluated using higher levels of sampling in the 1.6 mm (250 nl) Deep Chip. Specifically, candidate well identification was performed, following centrifugation, at various levels of z-plane sampling, including one (Z1), two (Z1+Z2), three (Z1+Z2+Z3), four (Z1+Z2+Z3+Z4), five (Z1+Z2+Z3+Z4+Z5), six (Z1+Z2+Z3+Z4+Z5+Z6) or seven (Z1+Z2+Z3+Z4+Z5+Z6+Z7) focal planes in the z-axis of the chip. Results for the candidate well quantification at the various sampling levels are provided in Table 5.

TABLE 5

1.6 mm (250 nl) Deep Chip

| Focal Planes in Z-axis | Post Centrifugation | Percent (%) of Z1 |
| --- | --- | --- |
| Z1 | 1192 | 100 |
| Z1 + Z2 | 1245 | 104.4 |
| Z1 + Z2 + Z3 | 1259 | 105.6 |
| Z1 + Z2 + Z3 + Z4 | 1260 | 105.7 |
| Z1 + Z2 + Z3 + Z4 + Z5 | 1270 | 106.5 |
| Z1 + Z2 + Z3 + Z4 + Z5 + Z6 | 1276 | 107 |
| Z1 + Z2 + Z3 + Z4 + Z5 + Z6 + Z7 | 1280 | 107.4 |

The above results demonstrate that, in some instances, centrifugation can be employed to increase the identification of candidate wells, i.e., wells containing the desired number of cells, which in the case evaluated above was limited to wells containing only a single cell. In some cases, post-dispense centrifugation may retrieve 20-25% more candidate wells as compared to similar candidate well identification performed without centrifugation. In addition, in some instances, where centrifugation is not employed, some of the wells identified as candidates containing a single cell may, in fact, be misidentified and actually contain two cells. Furthermore, in the dispense volumes employed in this example, centrifugation was seen to assist in removing air bubbles introduced after the cell dispense.

The above results also demonstrate that z-plane sampling levels above one or two Z-axis focal planes improved candidate well identification. Whereas a greater number of candidate wells were identified with the highest levels of z-plane sampling (e.g., Z5 and Z7), the increase in returns were diminishing as z-plane sampling increased and the results show that lower z-plane sampling, e.g., sampling of three z-planes, may provide sufficient sensitivity and specificity in many instances.

Figure 8:
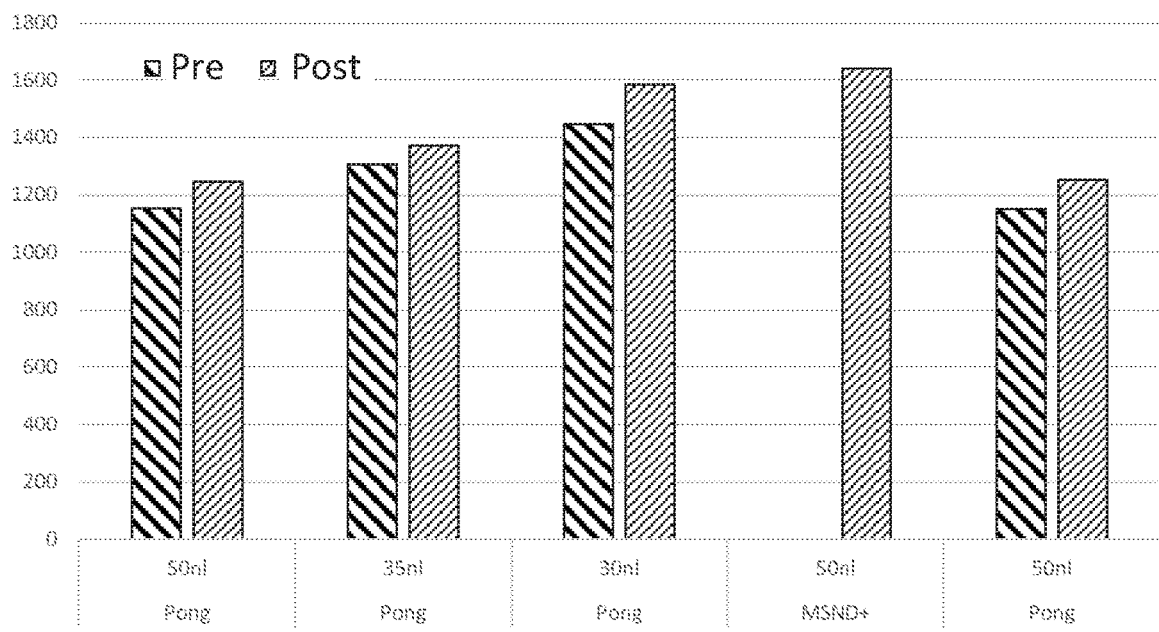
FIG. 8 depicts the results of candidate well quantification using various dispense volumes both with and without centrifugation of the multi-well chip.
Figure 9:
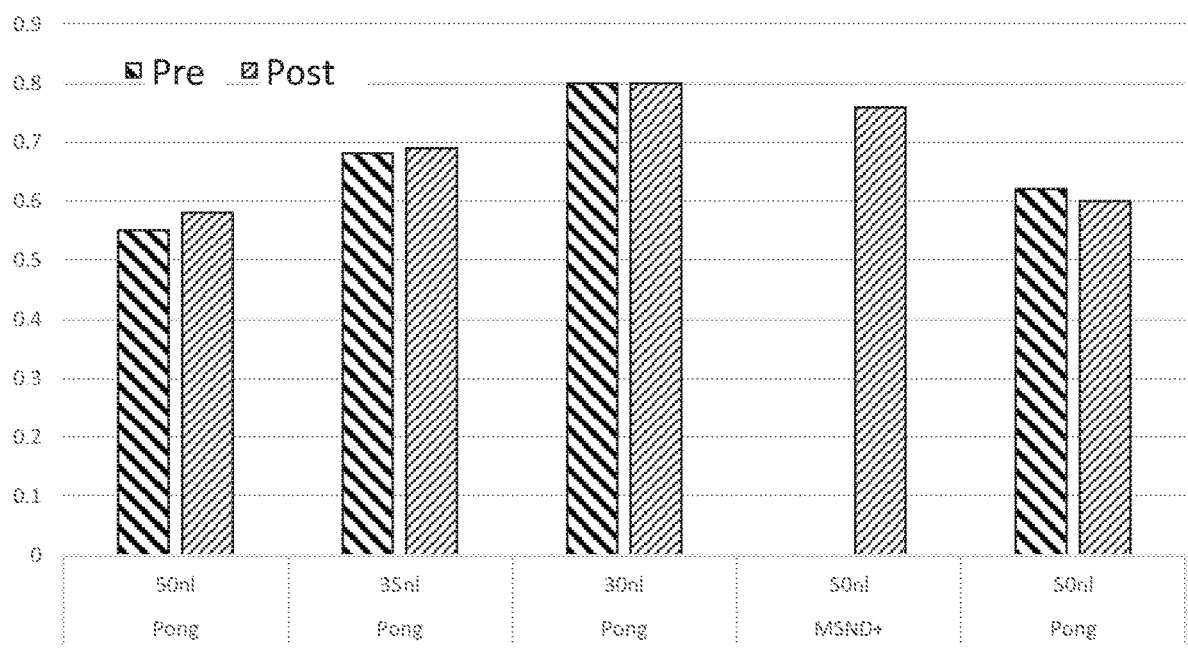
FIG. 9 provides percent Poisson calculated from the candidate well quantification as performed in FIG. 8.

To simultaneously test the influence of centrifugation and cell dispense volume on identification of candidate wells, candidate well identification was performed on a multi-z system ("Pong") using a range of cell dispense volumes (30 nl, 35nl and 50 nl) both before and after centrifugation of the multi-well device. As a reference, post-centrifugation candidate well identification was also performed using a MSND+ system at a cell dispense volume of 50 nl. The results of candidate wells quantification are provided in FIG. 8 and the corresponding percent of Poisson distribution at each tested condition is provided in FIG. 9.

These results reaffirm that, in some instances, centrifugation may be used to increase the identification of candidate wells. In the data provided, for example, the number of candidates increased by 5%-9% after centrifugation. The results also demonstrate that the number of candidate wells and the percent Poisson increase with decreasing dispense volumes. In this example specifically, the 30 nl dispense volume showed the best performance in terms of the number of candidates and the percent Poisson.

Example 2: Centrifugation can Reduce the Occurrence of Multiplets

Figure 10:
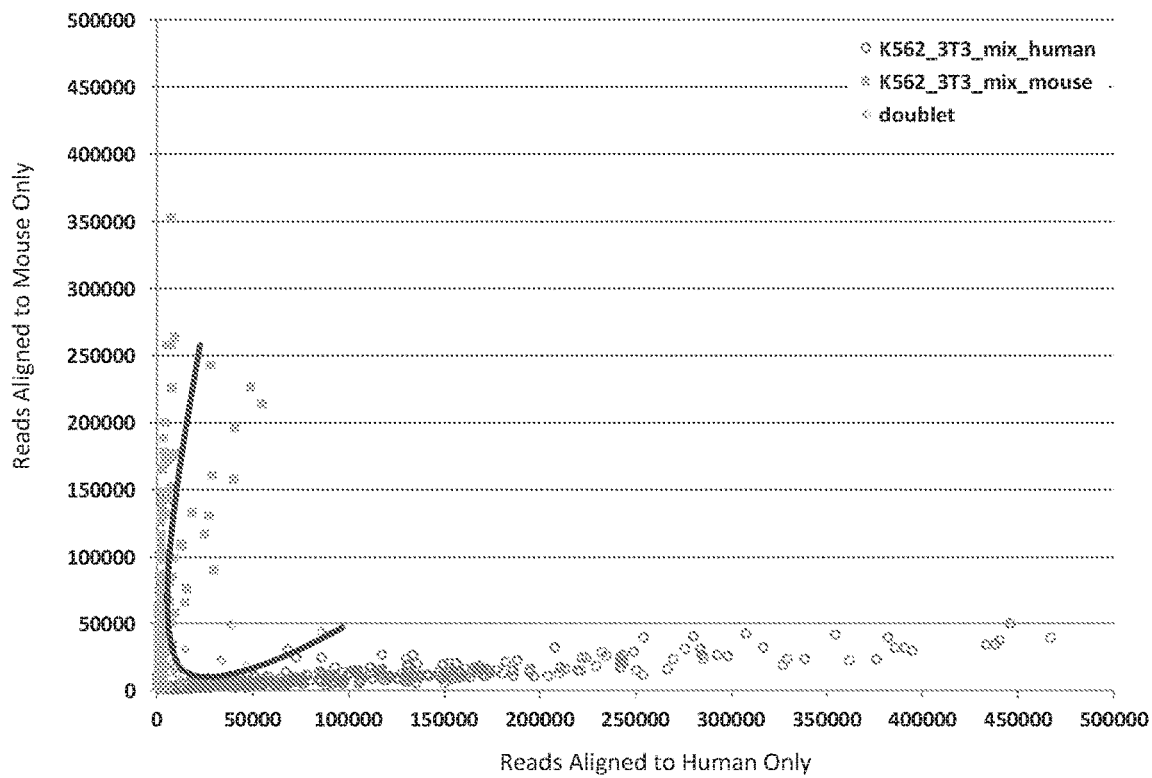
FIG. 10 depicts the relative multiplet rate, determined by sequencing alignment in a mixed species experiment, resulting from well identification performed without centrifugation.
Figure 11:
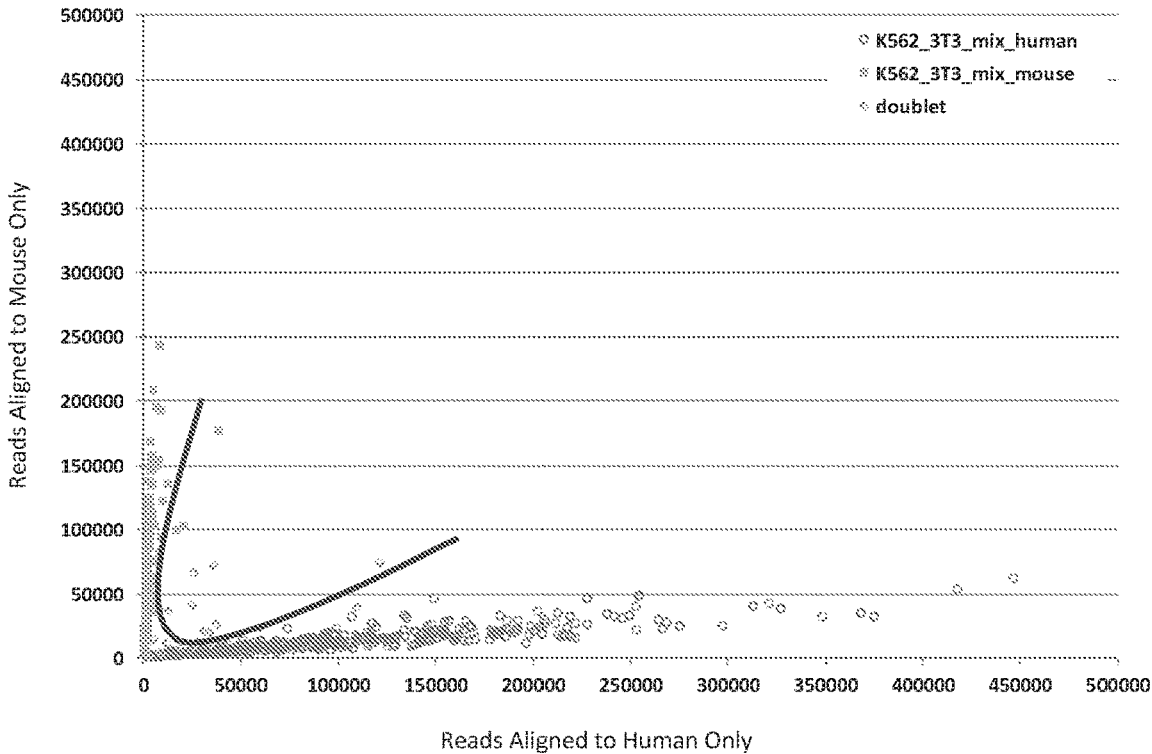
FIG. 11 depicts the relative multiplet rate, determined by sequencing alignment in a mixed species experiment, resulting from well identification performed with centrifugation.

The influence of centrifugation on the occurrence of multiplets (i.e., wells containing more than one cell) in candidate wells identified as containing single cells was assessed using a mixed species sequencing experiment. Specifically, human K-562 cells and mouse 3T3 cells mixed in equal ratio (1 cell per 50 nl) were dispensed into multi-well chips, candidate wells containing single cells were identified with and without prior centrifugation and the candidate wells were processed for RT-PCR and subsequently sequenced. The sequencing reads were aligned to the mouse and human genomes and the individual wells were retrospectively identified as containing reads that aligned only to mouse, only to human or both. Wells containing reads that aligned to both mouse and human were determined to contain multiplets. The sequencing read alignment data for pre-centrifugation (FIG. 10) and post-centrifugation (FIG. 11) samples is provided. The multiplet rate in the pre-centrifugation case was 5.8% whereas the multiplet rate in the post-centrifugation was lower, at 3.5%. These data demonstrate that, in some instances, centrifugation may be employed to decrease the occurrence of multiplets in identified single cell candidate wells.

Notwithstanding the appended claims, the disclosure is also defined by the following clauses:

1. A method of processing cell-containing wells of a multi-well chip, the method comprising:
   a) dispensing a volume of cell suspension into the wells of the multi-well chip;
   b) imaging the multi-well chip to acquire a plurality of images of the wells at multiple z-planes;
   c) generating a map of the multi-well chip, based on the acquired plurality of images, that identifies empty wells and cell-containing wells of the multi-well chip; and
   d) processing only the identified cell-containing wells of the multi-well chip.

2. The method of Clause 1, wherein generating the map comprises combining the acquired plurality of images to produce a composite image with extended depth of focus.

3. The method of Clauses 1 or 2, wherein the plurality of images comprises at least three z-planes.

4. The method of Clause 3, wherein the plurality of images comprises three to seven z-planes.

5. The method of any of the preceding Clauses, wherein the method further comprises pilot-imaging of a portion of the wells of the multi-well chip to deduce the multiple z-planes used in the imaging.

6. The method of Clause 5, wherein the pilot-imaging comprises determining a Zmax plane and a Zmin plane.

7. The method of Clause 6, wherein the multiple z-planes comprise the Zmax plane and the Zmin plane.

8. The method of Clauses 6 or 7, wherein the multiple z-planes comprise one to six z-planes between the Zmax plane and the Zmin plane.

9. The method of any of the preceding Clauses, wherein the imaging comprises simultaneous imaging of multiple wells.

10. The method of any of the preceding Clauses, wherein the map of the multi-well chip further identifies whether the cell-containing wells contain a single cell or a multiplet.

11. The method of Clause 10, wherein the method comprises processing only the cell-containing wells identified as containing a single cell.

12. The method of Clauses 10 or 11, wherein the map of the multi-well chip further identifies the number of cells present in each multiplet.

13. The method of Clause 12, wherein the method comprises processing multiplet-containing wells identified as containing two cells.

14. The method of any of the preceding Clauses, wherein the method further comprises centrifuging the multi-well chip after the dispensing and before the imaging.

15. The method of any of Clauses 1 to 13, wherein the method does not comprise centrifugation of the multi-well chip after the dispensing and before the imaging.

16. The method of any of the preceding Clauses, wherein the volume of cell suspension is 30 nl to 100 nl.

17. The method of Clause 16, wherein the volume of cell suspension is 30 nl to 50 nl.

18. The method of any of the preceding Clauses, wherein the number of wells present in the multi-well chip is 100 or more.

19. The method of any of the preceding Clauses, wherein the wells of the multi-well chip have a maximum volume of 250 nl or less.

20. The method of any of the preceding Clauses, wherein following the dispensing at least 1% of the wells of the multi-well chip are empty.

21. The method of any of the preceding Clauses, wherein following the dispensing at least 1% of the wells of the multi-well chip contain at least one cell.

22. The method of any of the preceding Clauses, wherein the processing comprises dispensing at least one reagent into the identified cell-containing wells.

23. The method of any of the preceding Clauses, wherein the processing comprises performing a nucleic acid amplification reaction in at least a portion of the identified cell-containing wells.

24. The method of Clause 23, wherein the processing comprises sequencing nucleic acid amplified from at least a portion of the identified cell-containing wells.

25. The method of any of the preceding Clauses, wherein the dispensing and imaging are performed by a dispense and image system assembly comprising a liquid dispensing component integrated with an image acquisition component.

26. A system comprising:
   a) a dispense and image system assembly comprising a liquid dispensing component and an image acquisition component; and
   b) a processor in communication with the dispense and image system assembly and a computer memory storing instructions that, when executed by the processor, cause the dispense and image system assembly to perform the steps of:
      i) dispense a volume of cell suspension into the wells of a multi-well chip;
      ii) image the multi-well chip to acquire a plurality of images of the wells at multiple z-planes; and
      iii) generate a map of the multi-well chip, based on the acquired plurality of images, that identifies empty wells and cell-containing wells of the multi-well chip.

27. The system of Clause 26, wherein the computer memory further comprises instructions to generate the map by combining the acquired plurality of images to produce a composite image with extended depth of focus.

28. The system of Clauses 26 or 27, wherein the computer memory further comprises instructions to perform pilot-imaging of a portion of the wells of the multi-well chip to deduce the multiple z-planes used in the imaging.

29. The system of any of Clauses 26 to 28, wherein the map of the multi-well chip further identifies whether the cell-containing wells contain a single cell or a multiplet.

30. The system of Clause 29, wherein the map of the multi-well chip further identifies the number of cells present in each multiplet.

31. The system of any of Clauses 26 to 30, wherein the computer memory further comprises instructions to store the generated map in the computer memory.

32. The system of any of Clauses 26 to 31, wherein the system further comprises a user interface, in communication with the processor and the computer memory.

33. The system of Clause 32, wherein the computer memory further comprises instructions to provide the generated map to a user via the user interface.

34. The system of Clauses 32 or 33, wherein the user interface allows for the user to instruct the system to process the identified cell-containing wells or a portion thereof.

35. The system of any of Clauses 26 to 34, wherein the computer memory further comprises instructions, that when executed by the processor, cause the system to further process only the identified cell-containing wells of the multi-well chip.

36. The system of Clause 35, wherein the instructions to further process only the identified cell-containing wells of the multi-well chip comprise instructions to dispense, using the liquid dispensing component, at least one reagent into only the identified cell-containing wells.

37. A method for imaging wells of a multi-well chip comprising:
   a) providing:
      i) a first multi-well device comprising a plurality of wells containing a first volume of aqueous solution, wherein at least 1% of said plurality of wells contain either only one or two cells, and
      ii) an image acquisition system capable of focusing and generating images at different z-planes, and
      iii) optionally a second multi-well device comprising a plurality of wells containing said first volume of an aqueous solution, wherein at least 1% of said plurality of wells contain either only one or only two cells;
   b) capturing a plurality of images from different z-planes above said multi-well device of a first portion of said plurality of wells using said image acquisition system configure with a first set of imaging parameters;
   c) determining the Zmax plane and the Zmin plane from said different z-planes, wherein said Zmax plane is the plane farthest from said multi-well device that contains a least one cell in focus, and wherein said Zmin plane is the plane closest to said multi-well device that contains at least one cell in focus;
   d) determining the minimum number of said different z-planes that are required to capture images from in order to generate a composite image that provides an in-focus image of all of the cells present in said first portion of said plurality of wells, wherein said minimum number of said different z-planes includes at least said Zmax and said Zmin planes; and
   e) performing at least one of the following:
      i) imaging, with said image acquisition system, a second portion of said plurality of wells of said multi-well device using only said minimum number of different z-planes; and/or
      ii) imaging at least a portion of said second multi-well device with an image acquisition system configured with said first set of imaging parameters, wherein said imaging uses only said minimum number of different z-planes.

38. The method of Clause 37, further comprising, in step e) generating a composite image from images taken at said minimum number of different z-planes.

39. The method of Clauses 37 or 38, further comprising, after step e) determining the number cells present in each of said wells in said second portion of said first multi-well device, and/or determining the number of cells present in each of said wells in said portion of said second multi-well device.

40. The method of any of Clauses 37 to 39, wherein said minimum number of different z-planes further includes one, two, three, or four z-planes between said Zmax and Zmin planes.

41. The method of any of Clauses 37 to 39, wherein said minimum number of different z-planes only includes said Zmax and said Zmin planes.

42. The method of any of Clauses 37 to 39, wherein said minimum number of different z-planes includes only said Zmax plane, said Zmin plane, and one other plane between said Zmax and Zmin planes.

43. The method of any of Clauses 37 to 42, wherein said imaging parameters comprises a first magnification.

44. The method of any of Clauses 37 to 43, wherein said imaging parameters comprise a first numerical aperture.

45. The method of any of Clauses 37 to 44, wherein said image acquisition system further comprises a light source.

46. The method of any of Clauses 37 to 45, wherein said cells are stained with one or more fluorescent stains.

47. The method of Clause 46, wherein said fluorescent stains are selected from Hoechst stain and Propidium Iodide.

48. The method of any of Clauses 37 to 47, wherein image acquisition system further comprises a liquid dispensing component configured to add said aqueous solution to said plurality of wells.

49. The method of Clause 48, wherein said liquid dispensing component is configured to dispense a dispense volume of said aqueous solution into each of said plurality of wells, wherein said aqueous solution comprises cells present in said aqueous solution at a concentration such that, on average X cell(s) is/are present in said dispense volume.

50. The method of Clause 49, wherein X is 0.02 or one.

51. The method of any of Clauses 37 to 50, wherein said plurality of wells in said first and/or second multi-well device is at least 100 wells.

52. The method of any of Clauses 37 to 51, wherein said second multi-well device is not provided.

53. The method of any of Clauses 37 to 52, wherein a dispensing map is generated that indicates which wells contain only a single cell, and which wells contain either zero or more than one cell.

54. The method of any of Clauses 37 to 53, wherein first volume of aqueous of solution is between 25 nl and 2 µl.

55. The method of any of Clauses 37 to 54, wherein each of said wells has a volume between 25 nl and 2 µl.

56. The method of Clause 55, wherein each of said wells has a volume between 50 nl and 500 nl.

57. A multi-purpose system comprising:
   a) a multi-well device securing component configured to secure a multi-well device in a fixed position, wherein said multi-well device comprises a plurality of wells;
   b) a dispense and image system assembly:
      i) a liquid dispensing component configured to dispense liquid into the wells of a multi-well device, and
      ii) an image acquisition component capable of focusing and generating images at different z-planes above said multi-well device,
   wherein said image acquisition component is attached to, or adjacent to, said liquid dispending component, and
   c) a movement component configured to move said dispense and image assembly with respect to said multi-well device such that, when said multi-well device is in said fixed position, most or all of said plurality of wells in said multi-well device:
      i) are able to receive liquid from said liquid dispensing component, and
      ii) are able to be imaged by said image acquisition component.

58. The system of Clause 57, wherein said liquid dispensing component is configured to dispense a dispense volume of liquid into each of said plurality of wells, wherein said liquid comprises cells present in said liquid at a concentration such that, on average X cell(s) is/are present in said dispense volume.

59. The system of Clause 58, wherein X is between 0.02 and one.

60. The system of any of Clauses 57 to 59, further comprising said multi-well device, and wherein said plurality of wells in said first multi-well device is at least 100 wells.

61. The system of any of Clauses 57 to 60, wherein said image acquisition component further comprises a light source.

62. The system of any of Clauses 57 to 61, wherein each of said plurality of wells has a volume between 25 nl and 2 µl.

63. The system of Clause 62, wherein each of said plurality of wells has a volume between 50 nl and 500 nl.

64. The system of any of Clauses 57 to 63, wherein said movement component comprises a first rail to move said dispense and image assembly in the X direction and a second rail to move said dispense and image assembly in the Y direction.

65. The system of any of Clauses 57 to 64, further comprising computer memory and a computer processor, wherein instructions on said computer memory control: i) the movement of said movement component, ii) the liquid dispensing of the dispense component, and iii) the image capture of the image acquisition component.

66. The system of any of Clauses 57 to 65, wherein said plurality of wells comprises at least 1000 wells.

67. A method comprising:
 a) providing:
  i) a multi-well device comprising a plurality of wells, and
  ii) a multi-well device securing component configured to secure a multi-well device in a fixed position, wherein said multi-well device comprises a plurality of wells,
  iii) multi-purpose system comprising:
   A) a dispense and image assembly comprising: I) a liquid dispensing component configured to dispense liquid into the wells of a multi-well device, and II) an image acquisition component capable of focusing and generating images at different z-planes above said multi-well device, wherein said image acquisition component is attached to, or adjacent to, said liquid dispending component, and
   B) a movement component configured to move said dispense and image assembly with respect to said multi-well device;
 b) placing said multi-well device in said securing component such said multi-well device is located at said fixed position; and
 c) activating said dispense and image assembly such that most or all of said plurality of wells in said multiwall device:
  i) receive cell-containing liquid from said liquid dispensing component such that at least 1% of said plurality of wells contains either only one or two cells, and
  ii) are imaged by said image acquisition component at a plurality of z-planes above said multi-well device thereby generating a plurality of images from different z-planes.

68. The method of Clause 67, further comprising: d) determining the Zmax plane and the Zmin plane from said different z-planes, wherein said Zmax plane is the plane farthest from said multi-well device that contains a least one cell in focus, and wherein said Zmin plane is the plane closest to said multi-well device that contains at least one cell in focus.

69. The method of Clause 68, further comprising: e) determining the minimum number of said different z-planes that are required to capture images from in order to generate a composite image that provides an in-focus image of all of the cells present in said plurality of wells, wherein said minimum number of said different z-planes includes at least said Zmax and said Zmin planes.

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A method of processing cell-containing wells of a multi-well chip, the method comprising:
 a) dispensing a volume of cell suspension into the wells of the multi-well chip;
 b) imaging the multi-well chip to acquire a plurality of images of the wells at multiple z-planes;
 c) generating a map of the multi-well chip, based on the acquired plurality of images, that identifies empty wells and cell-containing wells of the multi-well chip, wherein generating the map comprises combining the acquired plurality of images to produce a composite image with extended depth of focus; and
 d) processing only the identified cell-containing wells of the multi-well chip.

2. The method of claim 1, wherein the plurality of images comprises at least three z-planes.

3. The method of claim 1, wherein the method further comprises pilot-imaging of a portion of the wells of the multi-well chip to deduce the multiple z-planes used in the imaging.

4. The method of claim 1, wherein the imaging comprises simultaneous imaging of multiple wells.

5. The method of claim 1, wherein the map of the multi-well chip further identifies whether the cell-containing wells contain a single cell or a multiplet and the method comprises processing only the cell-containing wells identified as containing a single cell.

6. The method of claim 1, wherein the volume of cell suspension is 30 nl to 50 nl.

7. The method of claim 1, wherein the number of wells present in the multi-well chip is 100 or more.

8. The method of claim 1, wherein the processing comprises dispensing at least one reagent into the identified cell-containing wells.

9. The method of claim 1, wherein the processing comprises performing a nucleic acid amplification reaction in at least a portion of the identified cell-containing wells.

* * * * *